(12) United States Patent
Dolmer et al.

(10) Patent No.: US 12,377,124 B2
(45) Date of Patent: Aug. 5, 2025

(54) TOPICAL COMPOSITIONS COMPRISING VIABLE PROBIOTIC BACTERIA

(71) Applicant: Chr. Hansen A/S, Hoersholm (DK)

(72) Inventors: Mogens Dolmer, Hoersholm (DK); Mette Ingemann, Hoersholm (DK); Mette Winning, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 973 days.

(21) Appl. No.: 17/257,429

(22) PCT Filed: Jul. 3, 2019

(86) PCT No.: PCT/EP2019/067888
§ 371 (c)(1),
(2) Date: Dec. 31, 2020

(87) PCT Pub. No.: WO2020/007931
PCT Pub. Date: Jan. 9, 2020

(65) Prior Publication Data
US 2021/0220416 A1 Jul. 22, 2021

(30) Foreign Application Priority Data
Jul. 4, 2018 (EP) .................................. 18181691

(51) Int. Cl.
| | |
|---|---|
| A61K 35/747 | (2015.01) |
| A61K 9/00 | (2006.01) |
| A61K 9/16 | (2006.01) |
| A61K 35/745 | (2015.01) |
| A61K 45/06 | (2006.01) |
| A61K 47/06 | (2006.01) |
| A61K 47/14 | (2017.01) |
| A61K 47/44 | (2017.01) |

(52) U.S. Cl.
CPC .......... A61K 35/747 (2013.01); A61K 9/0014 (2013.01); A61K 9/16 (2013.01); A61K 35/745 (2013.01); A61K 45/06 (2013.01); A61K 47/06 (2013.01); A61K 47/14 (2013.01); A61K 47/44 (2013.01)

(58) Field of Classification Search
CPC ...... A61K 35/747; A61K 9/0014; A61K 9/16; A61K 35/745; A61K 45/06; A61K 47/06; A61K 47/14; A61K 47/44; A61K 35/744
See application file for complete search history.

(56) References Cited

U.S. PATENT DOCUMENTS

| | | | |
|---|---|---|---|
| 2008/0107699 A1 | 5/2008 | Spigelman et al. | |
| 2012/0156171 A1 | 6/2012 | Breton et al. | |
| 2013/0296165 A1* | 11/2013 | Harel | A61K 47/36 426/62 |
| 2017/0143621 A1* | 5/2017 | Baum | A61K 8/342 |
| 2017/0296610 A1 | 10/2017 | Ellington et al. | |
| 2017/0319703 A1* | 11/2017 | Haley | A61K 9/06 |
| 2020/0046837 A1 | 2/2020 | Graf | |
| 2021/0275613 A1 | 9/2021 | Dolmer et al. | |

FOREIGN PATENT DOCUMENTS

| | | | |
|---|---|---|---|
| CN | 1545936 A | 11/2004 | |
| EP | 2 364 712 A1 | 9/2011 | |
| KR | 20140128674 | * 11/2014 | ............. A61Q 19/02 |
| KR | 20140128675 | * 11/2014 | ............. A61Q 19/08 |
| WO | WO-2013/142792 A1 | 9/2013 | |
| WO | WO-2013/153358 A1 | 10/2013 | |
| WO | WO-2013/188626 A2 | 12/2013 | |
| WO | WO-2015/026235 A2 | 2/2015 | |
| WO | WO-2015/106175 A1 | 7/2015 | |
| WO | WO-2017/163217 A1 | 9/2017 | |
| WO | WO-2018002248 A1 | * 1/2018 | ........... A61K 35/747 |

OTHER PUBLICATIONS

Dao et al., AAPS PharmSciTech, 19(1): 60-78 (2018) (Year: 2018).*
Coronado Robles, Maria: "Probiotics promising cosmetic ingredient or marketing tool?" (Aug. 2016) Internet: URL https://www.researchgate.net/profile/Maria_Coronado/publication/308075735_Probiotics_-promising_cosmetic_ingredient-or-marketing-tool.pdf retrieved on Aug. 7, 2018.
Ding, W.K. et al; "Acid, Bile, and Heat Tolerance of Free and Microencapsulated Probiotic Bacteria"; Journal of Food Science, vol. 72, No. 9; Nov. 2007; pp. M446-M450.
Esse Skincare "Toner plus" (Aug. 2016) Internet: URL https://www.esseskincare.com/esse_product/toner-plus/ retrieved on Aug. 7, 2018.
Esse Skincare "Sensitive serum" Internet: URL https://www.esseskincare.com/esse_product/sensitive-serum/ retrieved on Aug. 7, 2018.
Proflora? Darm, retrieved from the internet: https://www.tetesept.de/produkte/gesundheit/erkaeltung/abwehrkraefte/proflora-darm-27036.htm, Oct. 1, 2016, pp. 1-5, retrieved Dec. 4, 2018.
Sharma et al., "Anti-aging effects of probiotics", J Drugs Dermatol., vol. 15, No. 1, pp. 9-12 (2016) Retrieved from the Internet: http://www.ncbi.nlm.nih.gov/pubmed/26741377 Retrieved on Aug. 7, 2018.
Sun, Xiaodong et al.; "Highly efficient treatment of aerobic vaginitis with simple acidic buffered gels: The importance of pH and buffers on the microenvironment of vaginas"; International Journal of Pharmaceutics, vol. 525; Apr. 13, 2017; pp. 175-182.

(Continued)

*Primary Examiner* — Kade Ariani
(74) *Attorney, Agent, or Firm* — Eric J. Fechter

(57) ABSTRACT

The present invention relates to topical compositions comprising at least $10^6$ CFU/g probiotic bacteria that remain viable in said composition for at least 6 months at 25° C./60% RH. The present invention also relates to methods for preparing such topical compositions, and a device suitable for long-term storage of viable probiotic bacteria. In addition, the present invention relates to the use of said composition.

18 Claims, 6 Drawing Sheets

(56) References Cited

OTHER PUBLICATIONS

Fonseca, Fernanda et al.; Chapter 24: "Freeze-Drying of Lactic Acid Bacteria"; Protein Chromatography: Methods and Protocols; 2015; pp. 477-488.
Her, Jae-Young et al.; "Preparation of probiotic powder by the spray freeze-drying method"; Journal of Food Engineering 150; Nov. 4, 2014; pp. 70-74.
FAO/WHO, "Health and Nutritional Properties of Probiotics in Food including Powder Milk with Live Lactic Acid Bacteria," Report of a Joint FAO/WHO Expert Consultation on Evaluation of Health and Nutritional Properties of Probiotics in Food Including Powder Milk with Live Lactic Acid Bacteria. Amerian Córdoba Park Hotel, Córdoba, Argentina Oct. 1-4, 2001, 34 pages.
"Esse Sensitive-Serum" (Jan. 2017) XP055539040, Retrieved from the Internet: http://shop.completeme.dk/shop/esse-sensitive-serum-1269p.html (Retrieved on Jan. 8, 2019). 7 pages.
Kurtmann et al., "Storage stability of freeze-dried *Lactobacillus acidophilus* (La-5) in relation to water activity and presence of oxygen and ascorbate", Cryobiology, vol. 58, (2009), pp. 175-180, XP025988708.
Passot et al., "Critical water activity and amorphous state for optimal preservation of lyophilised lactic acid bacteria", Food Chemistry 132, pp. 1699-1705 (2012) (avail online Jun. 15, 2011).
Fletcher, Eugene et al.; "Evolutionary engineering reveals divergent paths when yeast is adapted to different acidic environments"; Metabolic Engineering, vol. 39; Nov. 2, 2016; pp. 19-28.

\* cited by examiner

TOPICAL COMPOSITIONS COMPRISING VIABLE PROBIOTIC BACTERIA

CROSS-REFERENCE TO RELATED APPLICATIONS

The present application is the U.S. National Stage of International Application No. PCT/EP2019/067888, filed Jul. 3, 2019, and claims priority to European Patent Application No. 18181691.9, filed Jul. 4, 2018.

TECHNICAL FIELD OF THE INVENTION

It is well known in the art that probiotic bacteria in topical formulations do not survive in formulations that are moist and/or when the formulations are kept at high temperature.

The present invention relates to topical compositions comprising at least $10^6$ CFU/g bacteria of at least one probiotic bacterial strain that remain viable in said composition for at least 6 months at 25° C./60% RH. The present invention also relates to methods for preparing such topical compositions.

The present invention also relates to the use of said topical composition for providing at least $10^6$ CFU/g bacteria of at least one probiotic bacterial strain that remain viable in said topical composition for at least 6 months at 25° C./60% RH. Further, the present invention relates to a device that is suitable for long-term storage of viable probiotic bacteria—ready to use.

BACKGROUND OF THE INVENTION

Viability of probiotic bacteria is challenging to uphold in topical administration forms because probiotic bacteria are very easily broken down in moist environments (water activity between 0.40-0.90) and/or at ambient temperatures, such as 25° C. Also, probiotic bacteria in topical formulations may not survive in sufficient amount in formulations that comprise emulsifiers and/or preservatives.

This makes it very challenging to formulate topical compositions that maintain a stable and high level of probiotic bacteria that stay at the desired high level of probiotic bacteria for a considerable amount of time.

Several manufacturers have attempted to prepare topical formulations that comprise viable probiotic bacteria, but no products today provide viable probiotic bacteria in topical formulations. No commercial products provide viable probiotic bacteria in amounts above $10^6$ CFU/g that can be used by consumers to obtain the desired level of viable probiotic bacteria. Also, no products are available that can be stored for longer durations of time at ambient conditions and still maintain viable probiotic bacteria at a high level ready to use by the consumer.

Hence, there is a need in the art to provide topical formulations comprising viable probiotic bacteria after production, and after storage i.e. which are viable prior to application within assigned shelf life.

Hence, an improved topical formulation comprising viable probiotic bacteria would be advantageous, and in particular a topical formulation comprising viable probiotic bacteria after production, and after storage would be advantageous.

SUMMARY OF THE INVENTION

Thus, an object of the present invention relates to providing stable topical compositions comprising viable bacteria of at least one probiotic bacterial strain which compositions maintain a high level of probiotic bacteria for a considerable amount of time.

In particular, it may be seen as an object of the present invention to provide a topical composition comprising viable bacteria of at least one probiotic bacterial strain that solves the above-mentioned problems of the prior art with providing topical compositions that comprise viable probiotic bacteria after production, and after storage.

Thus, one aspect of the invention relates to a topical composition comprising viable bacteria of at least one probiotic bacterial strain and at least one hydrophobic compound, wherein at least $10^6$ CFU/g of the probiotic bacteria are viable in the topical composition for at least 6 months at 25° C./60% RH.

Another aspect of the present invention relates to a method of manufacturing a topical composition comprising providing at least one hydrophobic compound, adding viable bacteria of at least one probiotic bacterial strain to said hydrophobic compound to form said topical composition, wherein at least $10^6$ CFU/g of the probiotic bacteria are viable in the composition for at least 6 months at 25° C./60% RH.

Another aspect of the present invention relates to a use of a topical composition of the invention for providing at least $10^6$ CFU/g of viable bacteria of at least one probiotic bacterial strain after storage of the topical composition for at least 6 months at 25° C./60% RH.

Still another aspect of the present invention relates to a device comprising the topical composition of the invention.

Figure 1A:
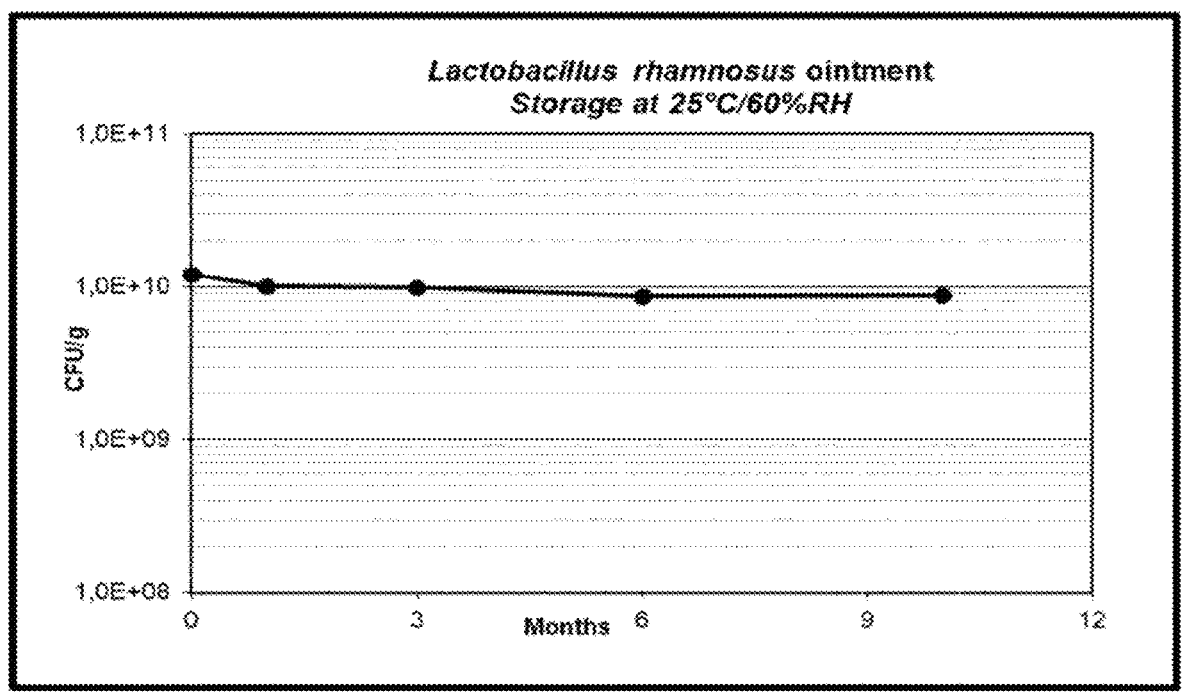
FIG. 1A shows stability of an ointment comprising *Lactobacillus rhamnosus* at 25° C.±3° C./60±5% RH.

The present invention will now be described in more detail in the following.

DETAILED DESCRIPTION OF THE INVENTION

Thus, one aspect of the invention relates to a topical composition comprising viable bacteria of at least one probiotic bacterial strain and at least one hydrophobic compound, wherein at least $10^6$ CFU/g of the probiotic bacteria are viable in the topical composition for at least 6 months at 25° C./60% RH. This aspect of the invention is demonstrated e.g. in FIG. 1A, which shows that an amount of at least $10^9$ CFU/g of said *Lactobacillus rhamnosus* is viable even at 10 months in the ointment.

Another aspect of the invention relates to a topical composition comprising
- viable bacteria of at least one probiotic bacterial strain selected from any strain belonging to the genus *Lactobacillus* and/or *Bifidobacterium*, and
- at least one hydrophobic compound selected from anionic emulsifying wax, candelilla wax, carnauba wax, cetyl palmitate, cocoa butter, gum arabic, hard fat, microcrystalline wax, nonionic emulsifying wax, paraffin, shea butter, synthetic beeswax, white wax, xantan gum, sunflower wax, mono glycerides, diglycerides, glyceryl behenate, glyceryl palmitostearate, glyceryl stearate and/or caprylic/capric/myristic/stearic triglyceride, ethyl oleate, evening primrose oil, grapeseed oil, hydrogenated vegetable (palm) oil, isopropyl isostearate, isopropyl myristate, isopropyl palmitate, jojoba (seed) oil, liquid lanolin, macademia oil, medium chain triglycerides, olive oil, paraffin oil/mineral oil, pomegrante oil, rapeseed oil, rice bran oil, rosehip oil, safflower oil, sesame oil, shea nut butter, soybean oil, sunflower oil, sweet almond oil, trimyristin, tripalmitin, tristearin, and avocado oil, and
- wherein said viable probiotic bacteria are provided in a dry composition, said dry composition comprising probiotic bacteria having a water activity of no more than 0.30, and
- wherein said dry composition comprises powdered viable probiotic bacteria having a diameter of no more than 300 μm.

In an embodiment of the invention, a topical composition is disclosed, wherein said viable bacteria of at least one probiotic bacterial strain is selected from a single strain or combination of strains of any one of *Lactobacillus rhamnosus, Lactobacillus paracasei* and *Bifidobacterium animalis* subsp *lactis*.

In an embodiment of the invention a topical composition is disclosed, wherein said hydrophobic compounds are hard fat, caprylic/capric/myristic/stearic triglyceride and one or more of oils and waxes that are fluid at room temperature selected from one or more of ethyl oleate, evening primrose oil, grapeseed oil, hydrogenated vegetable (palm) oil, isopropyl isostearate, isopropyl myristate, isopropyl palmitate, jojoba (seed) oil, liquid lanolin, macademia oil, medium chain triglycerides, olive oil, paraffin oil/mineral oil, pomegrante oil, rapeseed oil, rice bran oil, rosehip oil, safflower oil, sesame oil, shea nut butter, soybean oil, sunflower oil, sweet almond oil, trimyristin, tripalmitin, tristearin, and avocado oil.

In an embodiment of the invention a topical composition is disclosed, wherein said hydrophobic compounds are hard fat and caprylic/capric/myristic/stearic triglyceride and liquid paraffin.

In an embodiment of the invention a topical composition is disclosed, wherein said hydrophobic compounds are hard fat and caprylic/capric/myristic/stearic triglyceride.

In an embodiment of the invention a topical composition is disclosed, wherein said hydrophobic compound is liquid paraffin.

In an embodiment of the invention a topical composition is disclosed, wherein at least $10^6$ CFU/g of the probiotic bacteria are viable in the topical composition after 300 days of storage at 25° C./60% RH.

In an embodiment of the invention a topical composition is disclosed, wherein at least $10^7$ CFU/g of said probiotic bacteria are viable in the topical composition after 180 days of storage at 25° C./60% RH.

In an embodiment of the invention a topical composition is disclosed, wherein said topical composition comprises at least one active component, wherein said active component is selected from one or more of a compound selected from the group of vitamins, minerals, antiseptics, preservatives, sun protection agents or moisture sensitive agents.

In an embodiment of the invention a topical composition is disclosed, wherein said topical composition comprises less than 5% (w/w) water.

Another aspect of the invention relates to a method of manufacturing a topical composition according to the invention comprising
a) providing at least one hydrophobic compounds selected from anionic emulsifying wax, candelilla wax, carnauba wax, cetyl palmitate, cocoa butter, gum arabic, hard fat, microcrystalline wax, nonionic emulsifying wax, paraffin, shea butter, synthetic beeswax, white wax, xantan gum, sunflower wax, mono glycerides, diglycerides, glyceryl behenate, glyceryl palmitostearate, glyceryl stearate and/or caprylic/capric/myristic/stearic triglyceride, ethyl oleate, evening primrose oil, grapeseed oil, hydrogenated vegetable (palm) oil, isopropyl isostearate, isopropyl myristate, isopropyl palmitate, jojoba (seed) oil, liquid lanolin, macademia oil, medium chain triglycerides, olive oil, paraffin oil/mineral oil, pomegrante oil, rapeseed oil, rice bran oil, rosehip oil, safflower oil, sesame oil, shea nut butter, soybean oil, sunflower oil, sweet almond oil, trimyristin, tripalmitin, tristearin, and avocado oil, and
b) adding viable bacteria of at least one probiotic bacterial strain selected from any strain belonging to the genus *Lactobacillus* and/or *Bifidobacterium* to said hydrophobic compound to form said topical composition, and
wherein said viable probiotic bacteria are provided in a dry composition said dry composition comprising probiotic bacteria having a water activity of no more than 0.30, and
wherein said viable probiotic bacteria are powdered having a diameter of no more than 300 μm.

In an embodiment of the invention the method of manufacturing a topical composition is disclosed, wherein said viable bacteria of at least one probiotic bacterial strain is selected from one or more of a single strain or combination of strains of any one of *Lactobacillus rhamnosus, Lactobacillus paracasei* and *Bifidobacterium animalis* subsp *lactis*.

In an embodiment of the invention the method of manufacturing a topical composition is disclosed, wherein said topical composition comprises less than 5% (w/w) water.

In an embodiment of the invention the method of manufacturing a topical composition is disclosed, wherein at least $10^6$ CFU/g of said probiotic bacteria are viable in the topical composition after 300 days of storage at 25° C./60% RH.

In an embodiment of the invention the method of manufacturing a topical composition is disclosed, wherein at least $10^7$ CFU/g of said probiotic bacteria are viable in the topical composition after 180 days of storage at 25° C./60% RH.

In an embodiment of the invention a method of manufacturing a topical composition is disclosed, wherein said hydrophobic compounds are hard fat, caprylic/capric/myristic/stearic triglyceride and one or more of oils and waxes that are fluid at room temperature selected from one or more of ethyl oleate, evening primrose oil, grapeseed oil, hydrogenated vegetable (palm) oil, isopropyl isostearate, isopropyl myristate, isopropyl palmitate, jojoba (seed) oil, liquid lanolin, macademia oil, medium chain triglycerides, olive oil, paraffin oil/mineral oil, pomegrante oil, rapeseed oil, rice bran oil, rosehip oil, safflower oil, sesame oil, shea nut butter, soybean oil, sunflower oil, sweet almond oil, trimyristin, tripalmitin, tristearin, and avocado oil.

In an embodiment of the invention the method of manufacturing a topical composition is disclosed, wherein said hydrophobic compounds are hard fat, caprylic/capric/myristic/stearic triglyceride and sunflower oil.

In an embodiment of the invention the method of manufacturing a topical composition is disclosed, wherein said hydrophobic compounds are hard fat and caprylic/capric/myristic/stearic triglyceride.

In an embodiment of the invention the method of manufacturing a topical composition is disclosed, wherein said hydrophobic compound is liquid paraffin.

In an aspect of the invention a use of the topical composition is disclosed for providing a topical composition wherein at least $10^8$ CFU/g of the viable probiotic bacteria are viable in the topical composition after 300 days of storage at 25° C./60% RH.

In an embodiment of the invention, at least $10^7$ CFU/g, such as at least $10^8$ CFU/g, such as at least $10^9$ CFU/g of said probiotic bacteria are viable in the topical composition for at least 6 months at 25° C./60% RH, such as at least 24 months, such as at least 20 months, such as at least 16 months, such as at least 12 months, such as at least 8 months, such as at least 5 months, such as at least 4 months, such as at least 3 months, such as at least 2 months, such as at least 1 month, such as at least 14 days or, such as for 14 days to 24 months, such as for 14 days to 16 months, such as for 14 days to 8 months, such as 14 days to 4 months, such as 14 days to 2 months, such as 14 days to 1 month.

In a preferred embodiment, said probiotic bacteria are viable in the topical composition for at least 24 months at 25° C./60% RH, such as at least 20 months at 25° C./60% RH, such as at least 16 months at 25° C./60% RH, such as at least 12 months at 25° C./60% RH, such as at least 8 months at 25° C./60% RH, such as at for at least 6 months at 25° C./60% RH, such as at for at least 5 months at 25° C./60% RH, such as at for at least 4 months at 25° C./60% RH, such as at for at least 3 months at 25° C./60% RH, such as at for at least 2 months at 25° C./60% RH, such as at for at least 1 month at 25° C./60% RH, such as at least 14 days at 25° C./60% RH.

In an embodiment, a topical composition of the invention is provided, wherein said viable probiotic bacteria have a water activity of no more than 0.50, such as no more than 0.40, such as no more than 0.30, such as no more than 0.20, such as no more than 0.15, such as no more than 0.10. In a preferred embodiment, said water activity is no more than 0.3.

In an embodiment, a topical composition of the invention is provided, wherein said viable probiotic bacteria are anhydrous.

In an embodiment, a topical composition of the invention is provided, wherein said viable probiotic bacteria are substantially free from water.

In an embodiment, a topical composition of the invention is provided, wherein said viable probiotic bacteria are provided in a dry composition and optionally wherein the water activity of said dry composition is no more than 0.3, such as no more than 0.20, such as no more than 0.15. Preferably, the water activity of said dry compositions is no more than 0.3.

In an embodiment, a topical composition of the invention is provided, wherein said viable probiotic bacteria are provided in a dry composition and wherein said dry composition is anhydrous and/or substantially free from water.

In an embodiment, a topical composition of the invention is provided, wherein said dry composition has a diameter of no more than 500 μm, such as no more than 400 μm, such as no more than 300 μm, such as no more than 200 μm, such as no more than 150 μm, such as no more than 100 μm. In a preferred embodiment, said dry composition has a diameter of no more than 200 μm.

In an embodiment, a topical composition of the invention is provided, wherein said hydrophobic compound is selected from one or more of oils and waxes that are solid at room temperature and/or one or more of oils and waxes that are fluid at room temperature.

Oils and waxes may help thicken the composition of the invention.

In an embodiment, a topical composition of the invention is provided, wherein said one or more of oils and waxes that are solid at room temperature are selected from carnauba wax, glyceryl behenate, glyceryl palmitostearate, glyceryl stearate.

In an embodiment, a topical composition of the invention is provided, wherein said one or more hydrophobic compound is selected from carnauba wax, glyceryl behenate, glyceryl palmitostearate, glyceryl stearate.

In an embodiment, a topical composition of the invention is provided, wherein said one or more of oils and waxes that are solid at room temperature are selected from hard fat, caprylic/capric/myristic/stearic triglyceride.

In an embodiment, a topical composition of the invention is provided, wherein said one or more hydrophobic compound is selected from hard fat, caprylic/capric/myristic/stearic triglyceride.

In an embodiment, a topical composition of the invention is provided, wherein said one or more of oils and waxes that are fluid at room are selected from paraffin oil, almond oil, jojoba oil.

In an embodiment, a topical composition of the invention is provided, wherein said one or more hydrophobic compound is selected from paraffin oil, almond oil, jojoba oil.

In an embodiment, a topical composition of the invention is provided, wherein said one or more hydrophobic compound or is selected from hard fat, caprylic/capric/myristic/stearic triglyceride paraffin oil, almond oil, jojoba oil.

In an embodiment, a topical composition of the invention is provided, wherein said hydrophobic compounds are hard fat, caprylic/capric/myristic/stearic triglyceride and liquid paraffin.

In an embodiment, a topical composition of the invention is provided, wherein said topical composition comprises at least one active component.

In an embodiment, a topical composition of the invention is provided, wherein the at least one probiotic bacterial is selected from one or more of a single strain or combination of strains.

In an embodiment, a topical composition of the invention is provided, wherein the viable bacteria of at least one probiotic bacterial strain is selected from one or more of a single strain or combination of strains of any one of the strains of *Lactococcus lactis* subsp. *lactis* biovar. diacetylactis, *Lactococcus lactis* subsp. *cremoris*, *Lactococcuslactis* subsp. *lactis*, any strain belonging to the genus *Lactobacillus* including but not limited to *Lactobacillus acidophilus*, *Lactobacillus casei* subsp. *casei*, *L. casei* (Gynophilus), *L. coleohominis*, *Lactobacillus delbrueckii* subsp. *bulgaricus*, *Lactobacillus crispatus*, *Lactobacillus fermentum*, *L. fornicalis*, *L. gallinarum*, *Lactobacillus gasseri*, *Lactobacillus helveticus*, *Lactobacillus iners*, *Lactobacillus jensenii*, *Lactobacillus lactis*, *L. mucosae*, *L. paracasei*, *L plantarum*, *L. salivarius*, *L. reuteri*, *Lactobacillus rhamnosus*, *Lactobacillus salivarius*, *L. vaginalis*, strains belonging to the genus

*Bifidobacterium* including but not limited to *Bifidobacterium adolescentis, Bifidobacterium angulatum, Bifidobacterium animalis* subsp. *lactis, Bifidobacterium bifidum, Bifidobacterium breve, Bifidobacterium catenulatum, Bifidobacterium dentium, Bifidobacterium infantis, Bifidobacterium longum, Bifidobacterium magnum, Bifidobacterium pseudocatenulatum*, or from the genera of Akkermansia, Anaerostipes, Butyricicoccus, Christensenella, Clostridia, *Coprococcus, Dorea, Eubacterium, Faecalibacterium*, Cutibacterium, such as Cutibacterium *acnes*, or *Roseburia*, Staphylococcus, such as *Staphylococcus epidermis* or *Staphylococcus hominis, Weissella* viridescens, or the family Coriobacteriaceae.

In an embodiment, a topical composition of the invention is provided, wherein the viable bacteria of at least one probiotic bacterial strain is selected from one or more of a single strain or combination of strains of any one of *Bifidobacterium animalis* subsp. *lactis*, such as *Bifidobacterium animalis* subsp. *lactis*, such as *Bifidobacterium breve*, such as *Bifidobacterium infantis*, such as Cutibacterium *acnes*, such as *L. casei* (Gynophilus), such as *L. coleohominis*, such as *L. delbrueckii*, such as *L. fornicalis*, such as *L. gallinarum*, such as *L. iners*, such as *L. mucosae*, such as *L. paracasei*, such as *Lactobacillus paracasei* subsp. *paracasei*, such as *L. plantarum, L. rhamnosus*, such as *Lactobacillus rhamnosus*, such as *L. salivarius*, such as *L. reuteri*, such as *L. vaginalis*, such as *Staphylococcus epidermis* and such as *Staphylococcus hominis*, and such as *Weissella viridescens*.

In an embodiment, a topical composition of the invention is provided, wherein the viable bacteria of at least one probiotic bacterial strain is selected from a single strain or combination of strains of any one of strains *Bifidobacterium bifidum, Bifidobacterium breve, Bifidobacterium catenulatum, Bifidobacterium infantis, Bifidobacterium longum, Bifidobacterium pseudocatenulatum*, or from the genera of Cutibacterium, such as Cutibacterium *acnes*, or *Staphylococcus*, such as *Staphylococcus epidermis* or *Staphylococcus hominis*.

In presently preferred embodiments one, two, three, four, five, six, seven or eight different strains are present in a composition according to the invention.

In an embodiment, a topical composition of the invention is provided, wherein said hydrophobic compound is present in an amount of at least 80% w/w, such as at least 85% w/w, such as at least 90% w/w, such as at least 92% w/w, such as at least 94% w/w, such as at least 96% w/w, such as at least 98 w/w, such as at least 99% w/w, such as at least 99.9% w/w.

In an embodiment, a topical composition of the invention is provided, wherein said viable probiotic bacteria is present in an amount of at no more than 20% w/w or at least 0.1% w/w, such as no more than 19% w/w, such as no more than 17% w/w, such as no more than 15% w/w, such as no more than 13% w/w, such as no more than 11% w/w, such as no more than 9% w/w, such as no more than 7 w/w, such as no more than 5% w/w, such as no more than 4% w/w, such as no more than 3% w/w, such as no more than 2% w/w, such as no more than 1% w/w, such as no more than 0.5% w/w, such as at least 1% w/w, at least 2% w/w, at least 3% w/w, at least 4% w/w, at least 5% w/w, at least 6% w/w, at least 8% w/w, at least 10% w/w, at least 12% w/w, at least 14% w/w.

In an embodiment, a topical composition according to the invention is provided, wherein said topical composition is stable. This means that at least $10^6$ CFU/g of the bacteria of at least one probiotic bacterial strain are viable in the topical composition for at least 6 months at 25° C./60% RH or 30° C./75% RH or 5° C., such as for at least 5 months at 25° C./60% RH or 30° C./75% RH or 5° C., such as for at least 4 months at 25° C./60% RH or 30° C./75% RH or 5° C., such as for at least 3 months at 25° C./60% RH or 30° C./75% RH or 5° C., such as for at least 2 months at 25° C./60% RH or 30° C./75% RH or 5° C., such as for at least 1 month at 25° C./60% RH or 30° C./75% RH or 5° C., such as for at least 14 days at 25° C./60% RH or 30° C./75% RH or 5° C., such as for at least 7 days at 25° C./60% RH or 30° C./75% RH or 5° C., such as for at least 1 day at 25° C./60% RH or 30° C./75% RH or 5° C., such as for 14 days to 24 months, such as for 14 days to 16 months, such as for 14 days to 8 months, such as 14 days to 4 months, such as 14 days to 2 months, such as 14 days to 1 month.

In an embodiment, a topical composition of the invention is provided, wherein said topical composition has a viscosity of minimum 5000 cP (mPa·s), such as at least 6000 cP, such as at least 7000 cP, such as at least 8000 cP, such as at least 10000 cP, such as at least 20000 cP, such as at least 30000 cP, such as at least 40000 cP, such as at least 50000, such as at least 60000 cP.

In an embodiment, a topical composition of the invention is provided, wherein said topical composition comprises at least one water miscible solvent in amount of about 5-20% w/w, such as no more than 20% w/w, such as no more than 15% w/w, such as no more than 10% w/w, such as no more than 5% w/w and optionally at least one buffer. In a preferred embodiment of the invention, said at least one water miscible solvent is selected from C2-C5 alkyl alcohol, glycerol, polyethylene glycol, propylene glycol and C2-C5 glycol. In a particularly preferred embodiment, the water miscible solvent is one or more of water, glycerol, polyethylene glycol, and/or propylene glycol. In an even more preferred embodiment, said water miscible solvent is glycerol.

In an embodiment, a topical composition of the invention is provided, wherein said topical composition comprises at least one emulsifier. In an embodiment of the invention, said emulsifier is preferably selected from one or more of mono glycerides, diglycerides, triglycerides, citric acid esters of mono- and diglycerides.

In a preferred embodiment, a topical composition of the invention is provided, wherein said topical composition comprises at least one thickening agent. In an even more preferred embodiment, said thickening agent is selected from one or more of compounds of polyacrylic acid (carbomer) or derivatives hereof or other fast gelling polymers e.g. hyaluronic acid, gelatine, pectin and methylcellulose. Preferred thickening agents are selected from one or more of polymers, carbomer, poloxamer, PEG/macrogol and/or carboxylic acid. In an even more preferred embodiment, thickening agents are selected from one or more types of acrylic acid and C10-30 alkyl acrylate co-monomer and crosslinked polyacrylic acid copolymer.

In an alternative aspect of the invention, a topical composition is provided that comprises at least one moisture sensitive component which is not viable bacteria of at least one probiotic bacterial strain and at least one hydrophobic compound, wherein said at least one moisture sensitive agent is active in the topical composition for at least 24 months at 25° C./60% RH or 30° C./75% RH or 5° C., such as at least 20 months at 25° C./60% RH or 30° C./75% RH or 5° C., such as at least 16 months at 25° C./60% RH or 30° C./75% RH or 5° C., such as at least 12 months at 25° C./60% RH or 30° C./75% RH or 5° C., such as at least 8 months at 25° C./60% RH or 30° C./75% RH or 5° C., such as for at least 6 months at 25° C./60% RH or 30° C./75% RH or 5° C., such as for at least 5 months at 25° C./60% RH or 30° C./75% RH or 5° C., such as for at least 4 months at 25° C./60% RH or 30° C./75% RH or 5° C., such as for at least 3 months at 25° C./60% RH or 30° C./75% RH or 5° C., such as for at least 2 months at 25° C./60% RH or 30° C./75% RH or 5° C., such as for at least 1 month at 25° C./60% RH or 30° C./75% RH or 5° C., such as for at least 14 days at 25° C./60% RH or 30° C./75% RH or 5° C.

Another aspect of the present invention relates to a method of preparing/manufacturing a topical composition comprising providing at least one hydrophobic compound and adding viable bacteria of at least one probiotic bacterial strain to said hydrophobic compound to form said topical composition, wherein at least $10^6$ CFU/g of the bacteria of at least one probiotic bacterial strain are viable in the composition for at least 6 months at 25° C./60% RH or 30° C./75% RH or 5° C.

Preferably, said probiotic bacteria are viable in said composition in an amount of at least $10^7$ CFU/g, such as at least $10^8$ CFU/g, such as at least $10^9$ CFU/g, such as at least 5 months, such as at least 4 months, such as at least 3 months, such as at least 2 months, such as at least 1 month, such as at least 14 days, or, such as for 14 days to 24 months, such as for 14 days to 16 months, such as for 14 days to 8 months, such as 14 days to 4 months, such as 14 days to 2 months, such as 14 days to 1 month.

Preferably, said probiotic bacteria of at least one probiotic bacterial strain are viable in said composition for at least 6 months at 25° C./60% RH or 30° C./75% RH or 5° C., such as at for at least 5 months at 25° C./60% RH or 30° C./75% RH or 5° C., such as at for at least 4 months at 25° C./60% RH or 30° C./75% RH or 5° C., such as at for at least 3 months at 25° C./60% RH or 30° C./75% RH or 5° C., such as for at least 2 months at 25° C./60% RH or 30° C./75% RH or 5° C., such as for at least 1 month at 25° C./60% RH or 30° C./75% RH or 5° C., such as for at least 14 days at 25° C./60% RH or 30° C./75% RH or 5° C., or such as for 14 days to 24 months, such as for 14 days to 16 months, such as for 14 days to 8 months, such as 14 days to 4 months, such as 14 days to 2 months, such as 14 days to 1 month at 25° C./60% RH or 30° C./75% RH or 5° C.

In an embodiment of the invention, a method of manufacturing a topical composition according to the invention is provided, wherein viable bacteria of at least one probiotic bacterial strain are provided in a dry composition.

In an embodiment of the invention, a method of manufacturing a topical composition according to the invention is provided, wherein said at least one hydrophobic compound comprises at least one active component.

In an embodiment of the invention, a method of manufacturing a topical composition according to the invention is provided, wherein said hydrophobic compound is selected from one or more of oils and waxes that are solid at room temperature and/or one or more of oils and waxes that are fluid at room temperature.

In an embodiment of the invention, a method of manufacturing a topical composition according to the invention is provided, wherein said one or more of oils and waxes and/or emulsifier that are solid at room temperature are selected from carnauba wax, glyceryl behenate, glyceryl palmitostearate, glyceryl stearate.

Mono glycerids and diglycerids e.g. glyceryl behenate, glyceryl palmitostearate and glyceryl stearate are emulsifiers but they also behave as thickeners when mixed with oils or waxes.

In a preferred embodiment of the invention, a method of manufacturing a topical composition according to the invention is provided, wherein said one or more of oils and waxes that are solid at room temperature are selected from paraffin and one or more emulsifier is selected from glyceryl behenate and glyceryl stearate.

In an embodiment of the invention, a method of manufacturing a topical composition according to the invention is provided, wherein said one or more of oils and waxes that are fluid at room are selected from paraffin oil, almond oil and jojoba oil.

In an embodiment of the invention, a method of manufacturing a topical composition according to the invention is provided, wherein the at least one probiotic bacterial strain is selected from one or more of a single strain or combination of strains.

In an embodiment of the invention, a method of manufacturing a topical composition according to the invention is provided, wherein the viable bacteria of at least one probiotic bacterial strain is selected from one or more of a single strain or combination of strains of any one of the strains of *Lactococcus lactis* subsp. *lactis* biovar. diacetylactis, *Lactococcus lactis* subsp. *cremoris*, *Lactococcus lactis* subsp. *lactis*, any strain belonging to the genus *Lactobacillus* including but not limited to *Lactobacillus* acidophilus, *Lactobacillus casei* subsp. *casei*, *L. casei* (Gynophilus), *L. coleohominis*, *Lactobacillus delbrueckii* subsp. *bulgaricus*, *Lactobacillus crispatus*, *Lactobacillus fermentum*, *L. fornicalis*, *L. gallinarum*, *Lactobacillus* gasseri, *Lactobacillus* helveticus, *Lactobacillus* iners, *Lactobacillus* jensenii, *Lactobacillus lactis*, *L. mucosae*, *L. paracasei*, *L plantarum*, *L. salivarius*, *L. reuteri*, *Lactobacillus rhamnosus*, *Lactobacillus salivarius*, *L. vaginalis*, strains belonging to the genus *Bifidobacterium* including but not limited to *Bifidobacterium adolescentis*, *Bifidobacterium angulatum*, *Bifidobacterium animalis* subsp. *lactis*, *Bifidobacterium bifidum*, *Bifidobacterium breve*, *Bifidobacterium catenulatum*, *Bifidobacterium dentium*, *Bifidobacterium infantis*, *Bifidobacterium longum*, *Bifidobacterium magnum*, *Bifidobacterium pseudocatenulatum*, or from the genera of Akkermansia, Anaerostipes, Butyricicoccus, Christensenella, Clostridia, Coprococcus, Dorea, Eubacterium, Faecalibacterium, Cutibacterium, such as Cutibacterium *acnes*, or Roseburia, Staphylococcus, such as *Staphylococcus epidermis* or *Staphylococcus hominis*, *Weissella* viridescens, or the family Coriobacteriaceae.

In an embodiment of the invention, a method of manufacturing a topical composition according to the invention is provided, wherein the at least one probiotic bacterial strain is selected from one or more of a single strain or combination of strains of any one of *Bifidobacterium animalis* subsp. *lactis*, such as *Bifidobacterium animalis* subsp. *lactis*, such as *Bifidobacterium breve*, such as *Bifidobacterium infantis*, such as Cutibacterium *acnes*, such as *L. casei* (Gynophilus), such as *L. coleohominis*, such as *L. delbrueckii*, such as *L. fornicalis*, such as *L. gallinarum*, such as *L. iners*, such as *L. mucosae*, such as *L. paracasei*, such as *Lactobacillus paracasei* subsp. *paracasei*, such as *L. plantarum*, *L. rhamnosus*, such as *Lactobacillus rhamnosus*, such as *L. salivarius*, such as *L. reuteri*, such as *L. vaginalis*, such as *Staphylococcus epidermis* and such as *Staphylococcus hominis*, and such as *Weissella* viridescens.

In an embodiment of the invention, a method of manufacturing a topical composition of the invention is provided, wherein the viable bacteria of at least one probiotic bacterial strain is selected from a single strain or combination of strains of any one of strains *Bifidobacterium bifidum*, *Bifi-*

*dobacterium breve, Bifidobacterium catenulatum, Bifidobacterium infantis, Bifidobacterium longum, Bifidobacterium pseudocatenulatum*, or from the genera of Cutibacterium, such as Cutibacterium *acnes*, or *Staphylococcus*, such as *Staphylococcus epidermis* or *Staphylococcus hominis*.

In presently preferred embodiments one, two, three, four, five, six, seven or eight different strains are present in a composition according to the invention.

In an embodiment of the invention, a method of manufacturing a topical composition according to the invention is provided, wherein said hydrophobic compound is present in an amount of at least 90% w/w or no more than 99% w/w, such as at least 92% w/w, such as at least 94% w/w, such as at least 96% w/w, such as at least 98 w/w.

In an embodiment of the invention, a method of manufacturing a topical composition according to the invention is provided, wherein said viable probiotic bacteria is present in an amount of at least 15% w/w or no more than 5% w/w, such as at least 13% w/w, such as at least 11% w/w, such as at least 9% w/w, such as at least 7 w/w, such as at least 5% w/w, such as at least 4% w/w, such as at least 3% w/w, such as at least 2% w/w, such as at least 1% w/w.

In an embodiment of the invention, a method of manufacturing a topical composition according to the invention is provided, wherein said viable probiotic bacteria have a water activity of no more than 0.50, such as no more than 0.40, such as no more than 0.30, such as no more than 0.20, such as no more than 0.15, such as no more than 0.10.

In an embodiment of the invention, a method of manufacturing a topical composition according to the invention is provided, wherein said viable probiotic bacteria is provided in a dry composition having a diameter of no more than 500 μm, such as no more than 400 μm, such as no more than 300 μm, such as no more than 200 μm, such as no more than 150 μm, such as no more than 100 μm. In a preferred embodiment, said dry composition has a diameter of no more than 300 μm or 200 μm.

In an embodiment of the invention, a method of manufacturing a topical composition according to the invention is provided, wherein said topical composition is anhydrous or substantially free from water.

In an embodiment of the invention, a method of manufacturing a topical composition according to the invention is provided, wherein said topical composition is stable.

In another embodiment of the invention, a method of manufacturing a topical composition according to the invention is provided, comprising
  a) providing a composition of at least one hydrophobic compound and at least one water miscible solvent,
  b) providing viable bacteria of at least one probiotic bacterial strain,
  c) mixing the composition of step a) with the viable bacteria of step b) to form said topical composition, wherein at least $10^6$ CFU/g of the bacteria are viable in the composition for at least 6 months at 25° C./60% RH.

Preferably, said probiotic bacteria are viable in said composition in an amount of at least $10^7$ CFU/g, such as at least $10^8$ CFU/g, such as at least $10^9$ CFU/g, such as at least 5 months, such as at least 4 months, such as at least 3 months, such as at least 2 months, such as at least 1 month, such as at least 14 days, or, such as for 14 days to 24 months, such as for 14 days to 16 months, such as for 14 days to 8 months, such as 14 days to 4 months, such as 14 days to 2 months, such as 14 days to 1 month.

Preferably, said probiotic bacteria are viable in said composition for at least 6 months at 25° C./60% RH or 30° C./75% RH or 5° C., such as for at least 5 months at 25° C./60% RH or 30° C./75% RH or 5° C., such as for at least 4 months at 25° C./60% RH or 30° C./75% RH or 5° C., such as for at least 3 months at 25° C./60% RH or 30° C./75% RH or 5° C., such as for at least 2 months at 25° C./60% RH or 30° C./75% RH or 5° C., such as for at least 1 month at 25° C./60% RH or 30° C./75% RH or 5° C., such as at least 14 days at 25° C./60% RH or 30° C./75% RH or 5° C., or such as for 14 days to 24 months, such as for 14 days to 16 months, such as for 14 days to 8 months, such as 14 days to 4 months, such as 14 days to 2 months, such as 14 days to 1 month at 25° C./60% RH or 30° C./75% RH or 5° C.

In an embodiment of the invention, a method of manufacturing a topical composition according to the invention is provided, wherein said at least one water miscible solvent of step c) comprises
  (a) at least one active component
  (b) optionally at least one thickening agent
  (c) optionally at least one emulsifier/surfactant
  (d) optionally at least one buffer.

Another alternative aspect of the present invention relates to a method of manufacturing a topical composition comprising providing at least one hydrophobic compound, adding a dry composition of at least one moisture sensitive agent which is not viable probiotic bacteria to said hydrophobic compound to form said topical composition. In an alternative embodiment of the invention, said at least one moisture sensitive agent which is not viable probiotic bacteria is active in the topical composition for at least 24 months at 25° C./60% RH or 30° C./75% RH or 5° C., such as at least 20 months at 25° C./60% RH or 30° C./75% RH or 5° C., such as at least 16 months at 25° C./60% RH or 30° C./75% RH or 5° C., such as at least 12 months at 25° C./60% RH or 30° C./75% RH or 5° C., such as at least 8 months at 25° C./60% RH or 30° C./75% RH or 5° C., such as at for at least 6 months at 25° C./60% RH or 30° C./75% RH or 5° C., such as for at least 5 months at 25° C./60% RH or 30° C./75% RH or 5° C., such as at for at least 4 months at 25° C./60% RH or 30° C./75% RH or 5° C., such as at for at least 3 months at 25° C./60% RH or 30° C./75% RH or 5° C., such as at for at least 2 months at 25° C./60% RH or 30° C./75% RH or 5° C., such as at for at least 1 month at 25° C./60% RH or 30° C./75% RH or 5° C., such as at least 14 days at 25° C./60% RH or 30° C./75% RH or 5° C., or such as for 14 days to 24 months, such as for 14 days to 16 months, such as for 14 days to 8 months, such as 14 days to 4 months, such as 14 days to 2 months, such as 14 days to 1 month at 25° C./60% RH or 30° C./75% RH or 5° C.

Yet another aspect of the present invention relates to a use of the topical composition of the invention for providing a topical composition, wherein at least $10^6$ CFU/g of the bacteria of at least one probiotic bacterial strain are viable in the topical composition for at least 6 months at 25° C./60% RH or 30° C./75% RH or 5° C. Preferably, said probiotic bacteria are viable in said composition in an amount of at least $10^7$ CFU/g, such as at least $10^8$ CFU/g, such as at least $10^9$ CFU/g, such as at least 5 months, such as at least 4 months, such as at least 3 months, such as at least 2 months, such as at least 1 month, such as at least 14 days, or, such as for 14 days to 24 months, such as for 14 days to 16 months, such as for 14 days to 8 months, such as 14 days to 4 months, such as 14 days to 2 months, such as 14 days to 1 month. Preferably, said bacteria of at least one probiotic bacterial strain are viable in said composition for at least 6 months at 25° C./60% RH or 30° C./75% RH or 5° C., such as for at least 5 months at 25° C./60% RH or 30° C./75% RH or 5° C., such as for at least 4 months at 25° C./60% RH or 30° C./75% RH or 5° C., such as for at least 3 months at 25° C./60% RH or 30° C./75% RH or 5° C., such as for at least 2 months at 25° C./60% RH or 30° C./75% RH or 5° C., such as for at least 1 month at 25° C./60% RH or 30° C./75% RH or 5° C., such as at least 14 days at 25° C./60% RH or 30° C./75% RH or 5° C., or such as for 14 days to 24 months, such as for 14 days to 16 months, such as for 14 days to 8 months, such as 14 days to 4 months, such as 14 days to 2 months, such as 14 days to 1 month at 25° C./60% RH or 30° C./75% RH or 5° C.

Still another aspect of the present invention relates to a device comprising the topical composition of the invention.

In an embodiment, a device of the invention is provided, wherein said device is an aluminium tube with a re-attachable screw lid.

In an embodiment, a device of the invention is provided, wherein said device is a sachet or ampule.

In an embodiment, a device of the invention is provided, wherein said device is a plastic tube with a pump lid.

In an embodiment, a device of the invention is provided, wherein said device comprises a housing element and a delivery element.

Definitions

Prior to discussing the present invention in further details, the following terms and conventions will first be defined:

Probiotic Bacteria or Strain

In the present context, "probiotic bacteria or "bacteria of a probiotic bacterial strain" refers to a culture of microorganisms, such as bacteria, which, when applied to man or animal, beneficially affects the host (FAO/WHO, 2001, Health and Nutritional Properties of Probiotics in Food including Powder Milk with Live Lactic Acid Bacteria. Report of a Joint FAO/WHO Expert Consultation on Evaluation of Health and Nutritional Properties of Probiotics in Food Including Powder Milk with Live Lactic Acid Bacteria). Unless the context indicates otherwise, the terms "microorganism", "bacterium" and "probiotic" are used interchangeably. A bacterial "strain" as used herein refers to a bacterium which remains genetically unchanged when grown or multiplied.

In a preferred embodiment, the probiotic strain to be included in the dry composition or topical composition according to the invention is selected from one or more of the strains belonging to the genus *Bifidobacterium* including but not limited to *Bifidobacterium animalis* subsp. *lactis*, such as *Bifidobacterium animalis* subsp. *lactis*, *Bifidobacterium breve*, *Bifidobacterium infantis*, *Bifidobacterium bifidum*, *Bifidobacterium longum*, *Bifidobacterium catenulatum*, and *Bifidobacterium pseudocatenulatum*, strains belonging to the genus Cutibacterium, such as Cutibacterium *acnes*, any strain belonging to the genus *Lactobacillus* including but not limited to *L. casei* (Gynophilus), *L. coleohominis*, *L. delbrueckii*, *L. fornicalis*, *L. gallinarum*, *L. iners*, *L. mucosae*, *L. paracasei*, such as *Lactobacillus paracasei* subsp. *paracasei*, *L plantarum*, *L. rhamnosus*, such as *Lactobacillus rhamnosus*, *L. salivarius*, *L. reuteri*, *L. vaginalis*, strains of the genus *Staphylococcus*, such as *Staphylococcus epidermis* and *Staphylococcus hominis*, and *Weissella viridescens*.

In a preferred embodiment, the viable bacteria of at least one probiotic bacterial strain is selected from one or more of *Lactobacillus* and *Bifidobacterium*. In an even more preferred embodiment, the viable bacteria of at least one probiotic bacterial strain is selected from one or more of *Lactobacillus rhamnosus*, *Lactobacillus paracasei* and *Bifidobacterium animalis* subsp *lactis*.

Topical and Topical Composition

In the present context, "topical" is intended to mean application to a particular surface on or in the body, such as application to an external or internal body surface such as the skin or a mucous membrane, such as an ear, inside the nose, inside the mouth, lip, the urogenital area such as the urethral, vaginal, or rectal area, including the urethral opening, the vaginal opening and the anus. In one preferred embodiment, said topical application is intended for the urogenital area such as the urethral, vaginal, or rectal area, including the urethral opening, the vaginal opening and the anus. In another preferred embodiment, said topical application is intended for the skin.

In an embodiment of the invention, said skin or mucous membrane may be intact skin or mucous membrane. In another embodiment, said skin or mucous membrane may be compromised or damaged skin, e.g. suffering from dermatitis, such as atopic dermatitis, or having a burn, eczema, one or more psoriatic plaques, wounds, acne, sensitive skin, itching skin, vitiligo, rosacea, lichen sclerosis.

Thus, in the present context, "topical composition" is intended to mean a topical composition comprising at least one hydrophobic compound and viable bacteria of at least one probiotic bacterial strain that are capable of surviving in said topical composition until topical application, i.e. for at least 6 months at 25° C./60% RH or 30° C./75% RH or 5° C., such as for at least 5 months at 25° C./60% RH or 30° C./75% RH or 5° C., such as at least 4 months at 25° C./60% RH or 30° C./75% RH or 5° C., such as at least 3 months at 25° C./60% RH or 30° C./75% RH or 5° C., such as at least 2 months at 25° C./60% RH or 30° C./75% RH or 5° C., such as at least 1 month at 25° C./60% RH or 30° C./75% RH or 5° C., such as at least 14 days at 25° C./60% RH or 30° C./75% RH or 5° C., such as at least 7 days at 25° C./60% RH or 30° C./75% RH or 5° C., such as at least 1 day at 25° C./60% RH or 30° C./75% RH or 5° C., or such as for 14 days to 24 months, such as for 14 days to 16 months, such as for 14 days to 8 months, such as 14 days to 4 months, such as 14 days to 2 months, such as 14 days to 1 month at 25° C./60% RH or 30° C./75% RH or 5° C.

Said topical composition is suitable for topical use in a mammal, particularly a human. All components in the topical composition of the invention must be suitable for application to the body surface in question, i.e. they must be approved for topical application to the body surface in the concentrations used and/or be dermatologically and cosmetologically acceptable.

A topical composition according to the invention may be administered to a mammal, preferably a human, via a large range of topical administration forms. In the present context, topical compositions are epicutaneous, meaning that they are applied directly to the skin or mucous membranes.

A topical composition of the invention may be formulated as a cream, drop, foam, gel, lotion, ointment, paste, poultice, powder, salve, spray, thickened formulation, or unguent. In a preferred embodiment, the topical composition of the invention is selected from a cream, ointment, or a paste.

Dry Composition

In the present context, a "dry composition" is intended to mean a dry composition comprising probiotic bacteria that is powdered having a water activity of no more than 0.30, such as no more than 0.20, such as no more than 0.10 and a particle size diameter below 500 µm, preferably below 200 µm. Said dry composition may be prepared by conventional methods of freeze drying and/or spray drying followed by conventional grinding and sieving to obtain the desired particle size diameter below 500 µm. By using a diameter of below 500 µm, such as below 450 µm, such as below 400 µm, such as below 350 µm, such as below 300 µm, such as below 250 µm, such as below 200 µm, such as below 150 µm, such as below 100 µm, a topical composition with a good skin feel is obtained, that is comfortable for the user to apply topically and thus provides a pleasant sensory feeling upon application by consumers. In a preferred embodiment, the diameter of the dry composition is no more than 200 µm as this advantageously provides a pleasant skin feel for the consumer when using a topical composition of the invention.

A dry composition of the present invention comprises the bacteria in dried form, which can be obtained e.g. by freeze-drying, spray-drying or lyophilization.

Before the bacteria are dried, e.g. freeze-dried, they are generally mixed with a cryoprotectant in order to obtain a high viability. The term "a cryoprotectant" is used in the context of the present invention to refer to a substance that is able to improve the survival during freezing and/or drying and to improve the storage stability of bacteria. The cryoprotectant used herein preferably comprises a saccharide.

The saccharide may be a mono-, di-, oligo- or polysaccharide, or a mixture of at least two saccharides. Useful monosaccharides include glucose (also known as dextrose), fructose, ribose and galactose and useful disaccharides include among other sucrose, trehalose, maltose and lactose. The composition may comprise one or more mono- or disaccharides, such as one, two, or three or even more different saccharides.

As an example, the cryoprotectant may comprise a mixture of a disaccharide, such as sucrose, and a polysaccharide, such as maltodextrin.

The cryoprotectant may further comprise a peptide, protein, protein hydrolysate or a mixture thereof. Examples of peptides and proteins to be used are casein, pea, whey, albumin, soy protein, glutamic acid or gelatin, and any isolate or hydrolysate thereof. Other additives, e.g. antioxidants such as ascorbate, sodium citrate, propyl gallate may also be present.

Anhydrous/Substantially Free from Water

The terms "anhydrous" and "no available water" and "substantially free from water" are used interchangeably. A dry composition of the present invention can be defined as having "no available water" and "substantially free from water", and these words are used interchangeably and are intended to mean that the water present in the topical composition of the invention comprising viable probiotic bacteria of at least one probiotic bacterial strain is not able to solvate the probiotic bacteria, because the water is present in too small an amount. This also means that the water activity is no more than 0.30.

In the present context, "anhydrous" viable bacteria of at least one probiotic bacterial strain means viable probiotic bacteria which are essentially free of water. Particularly, for such viable probiotic bacteria a significant amount of water has not been added, and the amount of un-bound water in the viable probiotic bacteria is very low. Some components in the probiotic bacteria may include some bound water, i.e. water of crystallisation in the form of hydrates or sugars that have water bound to them. This water is however not immediately available for participating in hydrolysis reactions with water sensitive components such as freeze dried viable probiotic bacteria. In preferred embodiments the anhydrous viable probiotic bacteria of the present invention comprises less than 5% (w/w) water, such as less than 4% (w/w) water, 3% (w/w), 2% (w/w), 1.5% (w/w), 1% (w/w), 0.5% (w/w), such as less than 0.2% (w/w) water as compared to total composition weight. Preferably the amount of added water to the anhydrous viable probiotic bacteria is less than 3% (w/w), such as less 2% (w/w), 1% (w/w), 0.5% (w/w), such as less than 0.1% (w/w). Preferably said viable probiotic bacteria will be present in a dried form.

Stable

The term "stable" is intended to mean that the topical composition of the invention maintains a level of viable probiotic bacteria at a stable level for the entire duration of the storage time. This means that at least $10^6$ CFU/g of the probiotic bacteria are viable in the topical composition for at least 6 months at 25° C./60% RH or 30° C./75% RH or 5° C., such as for at least 5 months at 25° C./60% RH or 30° C./75% RH or 5° C., such as at least 4 months at 25° C./60% RH or 30° C./75% RH or 5° C., such as at least 3 months at 25° C./60% RH or 30° C./75% RH or 5° C., such as at least 2 months at 25° C./60% RH or 30° C./75% RH or 5° C., such as at least 1 month at 25° C./60% RH or 30° C./75% RH or 5° C., such as at least 14 days at 25° C./60% RH or 30° C./75% RH or 5° C., such as at least 7 days at 25° C./60% RH or 30° C./75% RH or 5° C., such as at least 1 day at 25° C./60% RH or 30° C./75% RH or 5° C. Preferably, said probiotic bacteria are viable in said composition in an amount of at least $10^7$ CFU/g, such as at least $10^8$ CFU/g, such as at least $10^9$ CFU/g, such as at least 5 months, such as at least 4 months, such as at least 3 months, such as at least 2 months, such as at least 1 month, such as at least 14 days, or, such as for 14 days to 24 months, such as for 14 days to 16 months, such as for 14 days to 8 months, such as 14 days to 4 months, such as 14 days to 2 months, such as 14 days to 1 month.

Preferably, said probiotic bacteria are viable in said composition for 14 days to 24 months, such as for 14 days to 16 months, such as for 14 days to 8 months, such as 14 days to 4 months, such as 14 days to 2 months, such as 14 days to 1 month at 25° C./60% RH or 30° C./75% RH or 5° C.

Water Activity

In the present context, "water activity" or "$a_w$" is the partial vapor pressure of water in a substance divided by the standard state partial vapor pressure of water. Pure distilled water has a water activity of exactly one. As temperature increases, $a_w$ typically increases. The water activity of the probiotic bacteria according to the invention is no more than 0.30, such as no more than 0.20, such as no more than 0.15. Preferably, the water activity is no more than 0.30 and preferably said viable probiotic bacteria will be present in a dried form having a water activity of no more than 0.30.

Viable/Viable Probiotic Bacteria

In the present context, "viable" is intended to mean that the probiotic bacteria of the present invention are capable of normal growth and development i.e. viable bacteria of at least one probiotic bacterial strains mean that the probiotic bacteria are viable and thus capable of normal growth and development. In the present invention, the viable probiotic bacteria have been dried in a way so as to leave the probiotic bacteria viable. Several conventional ways of preparing viable probiotic bacteria are well known in the art.

CFU

In the present context, CFU is intended to mean "colony forming units" and Colonic Forming Units per g product (CFU/g), can be measured as disclosed under the Examples section.

Viable in the Topical Composition

In the present context, "viable in the topical composition" is intended to mean that probiotic bacteria remain viable in the topical composition in an amount of at least $10^6$ CFU/g for at least 6 months at 25° C./60% RH or 30° C./75% RH or 5° C., such as for at least 5 months at 25° C./60% RH or 30° C./75% RH or 5° C., such as at least 4 months at 25° C./60% RH or 30° C./75% RH or 5° C., such as at least 3 months at 25° C./60% RH or 30° C./75% RH or 5° C., such as at least 2 months at 25° C./60% RH or 30° C./75% RH or 5° C., such as at least 1 month at 25° C./60% RH or 30° C./75% RH or 5° C., such as at least 14 days at 25° C./60% RH or 30° C./75% RH or 5° C., such as at least 7 days at 25° C./60% RH or 30° C./75% RH or 5° C., such as at least 1 day at 25° C./60% RH or 30° C./75% RH or 5° C. or, such as for 14 days to 24 months, such as for 14 days to 16 months, such as for 14 days to 8 months, such as 14 days to 4 months, such as 14 days to 2 months, such as 14 days to 1 month at 25° C./60% RH or 30° C./75% RH or 5° C.

RH

In the present context, "RH" is intended to mean "Relative humidity" and it is the ratio of the partial pressure of water vapor to the equilibrium vapor pressure of water at a given temperature.

Hydrophobic Compounds

In the present context, "hydrophobic compounds" as used herein are compounds that are nonpolar and, thus, prefer other neutral molecules and nonpolar solvents. Examples of hydrophobic compounds include the alkanes, oils, fats, and greasy substances in general.

Oils and Waxes

In the present context, "oils and waxes", being a subgroup of hydrophobic compounds as used herein, are vegetal and/or mineral oils and/or waxes. In an embodiment, oils and vaxes to be used in the composition of the invention are selected from oils and waxes that are solid or fluid at room temperature.

Oils and waxes that are fluid at room temperature may be selected from one or more of ethyl oleate, evening primrose oil, grapeseed oil, hydrogenated vegetable (palm) oil, isopropyl isostearate, isopropyl myristate, isopropyl palmitate, jojoba (seed) oil, liquid lanolin, macadamia oil, medium chain triglycerides, olive oil, paraffin oil/mineral oil, pomegrante oil, rapeseed oil, rice bran oil, rosehip oil, safflower oil, sesame oil, shea nut butter, soybean oil, sunflower oil, sweet almond oil, trimyristin, tripalmitin, tristearin, and avocado oil. In a preferred embodiment, the oil or wax that is fluid at room temperature is selected from one or more of paraffin oil, almond oil and jojoba oil. In an even more preferred embodiment, the oil or wax that is fluid at room temperature is paraffin oil. Paraffin oil is also called liquid paraffin.

Oils and waxes that are solid at room temperature as used herein are selected from one or more of anionic emulsifying wax, candelilla wax, carnauba wax, cetyl palmitate, cocoa butter, gum arabic, hard fat, microcrystalline wax, nonionic emulsifying wax, paraffin, shea butter, synthetic beeswax, white wax, xantan gum, sunflower wax, mono glycerides, diglycerides, glyceryl behenate, glyceryl palmitostearate, glyceryl stearate and/or caprylic/capric/myristic/stearic triglyceride.

In a preferred embodiment, the oil or wax that is solid at room temperature is selected from one or more of anionic emulsifying wax, hard fat, caprylic/capric/myristic/stearic triglyceride, candelilla wax, carnauba wax, microcrystalline wax, nonionic emulsifying wax, synthetic beeswax, mono glycerides, diglycerides, white wax and/or sunflower wax. In an even more preferred embodiment, the oil or wax that is solid at room temperature is selected from one or more of carnauba wax, hard fat, caprylic/capric/myristic/stearic triglyceride, glyceryl behenate, glyceryl palmitostearate and/or glyceryl stearate.

It should be noted that monoglycerides, diglycerides, glyceryl behenate, glyceryl palmitostearate and/or glyceryl stearate also act as solid emulsifiers when mixed with one or more oils and/or waxes.

In an even more preferred embodiment, a combination of fluid and solid oils and waxes are used, such as at least one solid oil combined with at least one fluid oil, such as at least two fluid oils and at least one solid oil or vice versa, such as at least three fluid oils and at least one solid or vice versa.

Active Components

In the present context, an "active component" is defined as one or more of a compound selected from the group of vitamins, minerals, antiseptics, preservatives, sun protection agents, moisture sensitive agents or various other agents. Vitamins may be selected from vitamin A, such as retinol/retinyl esters, vitamin B such as nicotinamide/niacin. Minerals may be selected from zinc.

Antibacterials/antiseptics may be selected from salicylic acid, azelaic acid benzoyl peroxide. Antiseptics to be used for the present invention should not kill or inhibit growth of the probiotic bacteria of the present invention when the probiotic bacteria are in a dry state i.e. having a water activity of no more than 0.3. Also, in the topical composition of the present invention, the antiseptics should not kill or inhibit growth of the probiotic bacteria.

Preservatives may be selected from preservatives well known in the art, such as e.g. sorbic acid, sodium sorbate, benzoic acid, sodium benzoate and benzoates, hydroxybenzoate, lactic acid, propionic acid, sodium propionate and parabens, such as one or more of methylparaben, ethylparaben, propylparaben, butylparaben, heptylparaben, isobutylparaben, isopropylparaben, benzylparaben and their sodium salts. In an embodiment of the invention, the preferred preservative is selected from one or more of sorbic acid or benzoic acid. Sun protection agents may be selected from p-Aminobenzoic acid, Padimate O, Phenylbenzimidazole sulfonic acid, Cinoxate, Dioxybenzone, Oxybenzone, Homosalate, Menthyl anthranilate, Octocrylene, Octyl methoxycinnamate, Octyl salicylate, Sulisobenzone, Trolamine salicylate, Avobenzone, Ecamsule, Titanium dioxide, Zinc oxide, 4-Methylbenzylidene camphor, Parsol Max, Tinosorb M, Parsol Shield, Tinosorb S, Tinosorb A2B, Neo Heliopan AP, Mexoryl XL, Benzophenone-9, Uvinul T 150, Uvinul A Plus, Uvasorb HEB, Parsol SLX, Amiloxate.

Various other agents may be selected from cranberry, tea tree oil or extracts such as extracts from aloe vera, camomile, milk thistle, walnut, witch hazel, burdock dry, liquorice dry or sage.

Moisture sensitive agents/active water sensible agents may be selected from proteinases/protease enzymes such as papain, bromelain and actinidin. Moisture sensitive agents are defined as compounds that will lose their effect upon contact with water.

Percent Weight/Weight or % (w/w)

In the present context "percent weight/weight" or "% (w/w)" are used interchangeably and indicates the weight percentage of a component or ingredient as compared to total composition weight, i.e. the weight of the finished composition unless otherwise indicated. In certain cases, it may refer to the weight percentage as compared to an intermediate composition.

Viscosity

The dynamic viscosity of the hydrophobic compound should be medium to high and firm, i.e. preferably having a viscosity above 2500 cP (mPa-s) when measured at 25° C., such as above 3000 cP (mPa-s), such as above 4000 cP (mPa-s), such as above 5000 cP (mPa-s). The viscosity is measured using a HR-1 Discovery Hybrid Rheometer from TA Instruments, with a 40 mm parallel plate on Peltier plate steel, with a constant shear rate at 2.0 s$^{-1}$.

In another embodiment the dynamic viscosity of the hydrophobic compound should be low to medium and fluid, i.e. preferably having a viscosity less than 2500 cP (mPa-s) when measured at 20 rpm at 20° C./60% RH, such as less than 2400 cP (mPa-s), such as less than 2200 cP (mPa-s), such as less than 2000 cP (mPa-s). When the hydrophobic compound is mixed with the dry composition, the viscosity of the mixture increases 3-1000 times and becomes medium to high, i.e. 2500 cP (mPa-s) or more when measured at 20 rpm at 20° C./60% RH, more preferably above 5000 cP (mPa-s) when measured at 20 rpm 20° C./60% RH. The viscosity is measured using a conventional Brookfield Laboratory Viscometer.

Water Miscible Solvent

In the present context, "water miscible solvent" is a solvent which may be mixed with water without any phase separation. Water miscible solvents particularly include hydrophilic solvents. Such solvents include for example lower alkyl alcohols, hydrophilic organic solvents and water. A hydrophile is a molecule or other molecular entity that is attracted to water molecules and tends to be dissolved by water. In the present context, "alkyl alcohol" is in the broadest sense an organic alcohol consisting of a branched or linear alkyl chain and one or more hydroxyl groups attached thereto. Thus, in a preferred embodiment the water miscible solvent is selected from the group consisting of a C2-C5 alkyl alcohol, glycerol, polyethylene glycol, propylene glycol and C2-C5 glycol. In a particularly preferred embodiment, the water miscible solvent is one or more of water, glycerol, polyethylene glycol and/or propylene glycol. In a preferred embodiment, an acid or base can be added to the water miscible solvent to adjust the pH.

Emulsifiers

In the present context, an "emulsifier" is a compound capable of lowering the surface tension (or interfacial tension) between two liquids, or between a liquid and a solid. According to the invention an emulsifier capable of lowering the surface tension between one or more water miscible solvents of the invention and one or more of hydrophobic compounds of the invention to provide the topical composition as defined herein. Surfactants may act as detergents, wetting agents, emulsifiers, foaming agents, and dispersants, and they are selected from one or more of alkyl (C12-15) benzoate, capryl/capramidopropyl betaine, ceteareth-25, cetmacrogol, emulsifying wax, cetomacrogol 1000, cetostearyl alcohol, cetylalcohol, cetyl esters wax, cetyl palmitate, cetyl PEG/PPG-10/1 dimethicone, emulsifying wax, ethyl oleate, monoglycerides e.g. glycerol monosterate, glycerol monopalmitate, glycerol monooelate, diglycerides e.g. glycerol dioleate, glycerol dipalmitate, glycerol disterate, mono- and diglycerides e.g. glyceryl behenate, glycerol stearate, glycerol laurate, glycerol palmitate, mono-, di- and triglycerides e.g. glyceryl behenate, glycerol stearate, glycerol laurate, glycerol palmitate, hydrogenated cocoglycerides, macrogol cetostearyl ether, macrogol glycerol ricinoleate, macrogol lauryl ether, macrogol oleyl ether, macrogol stearate, macrogol stearyl ether, methyl glucose isostearate, PEG-120 methyl glucose dioleate, PEG-100 stearate, polyglyceryl isosterate, polyglyceryl oleate, polyoxypropylene stearyl ether, polysorbate 20, polysorbate 60, polysorbate 80, propyleneglycol dicaprylate/caprate, ricinoleamidopropyl betaine, sorbitan isostearate, sorbitan laurate, sorbitan oleate, sorbitan sesquilate, sorbitan stearate, sorbitan trioleate, steareth-2, stearyl alcohol, sucrose stearate, sucrose palmitate, sucrose behenate, sucrose myristate, sucrose laurate, sucrose oleate, sucrose erucate, sucrose ester of mixed fatty acids, undecylenamidopropyl betaine, citric acid esters of the mono- and diglycerides, citrilated glycerol monooelate, citrilated glycerol monostearate, lactic acid esters of mono- and diglycerides, high molecular weight copolymers of acrylic acid, $C_{10}$-$C_{30}$ alkyl acrylate crosslinked with allyl pentaerythritol, glyceryl behenate, glyceryl behenate, and/or glycerol stearate. In a preferred embodiment, the emulsifier is selected from one or more of mono glycerides, diglycerides, triglycerides, citric acid esters of mono- and diglycerides. In a preferred embodiment, the emulsifier is added to the water miscible solvent only.

Buffer

In the present context, a buffer is an acid or base used to maintain the acidity (pH) of a solution near a chosen value after the addition of another acid or base. Hence, the buffer balances the pH of a topical composition of the invention to make the composition less irritating. The one or more buffers is/are selected from buffers with a pKa in the range of 2-9, such as 2-7. Presently preferred buffers are monovalent cations. In an even more preferred embodiment of the invention, the one or more buffers is/are selected from monovalent carbonates, ascorbates, phosphates, malates, citrates, tartrates, such as sodium bicarbonate, sodium malate, sodium tartrate, potassium tartrate, sodium hydrogen carbonate, and tri sodium citrate dehydrate. However, other ways of adjusting the pH in the topical composition may also be feasible. As an example, triethanolamine and sodium hydroxide may be useful for certain embodiments.

In an embodiment, one or more buffers is/are present in the dry composition and/or added to the water miscible solvent when desired to control the pH at a certain level. In a preferred embodiment of the invention, one or more buffers is/are present in the final product i.e. the topical composition of the invention.

A buffer is important for the function of the carbomer if present in the present invention, as a carbomer has a low viscosity when the pH is low, as carbomers then do not swell (absorb and retain water). When the pH increases, the carbomer swells and thus increases the viscosity. Hence, a buffer in the presence of a carbomer provides for a possibility of controlling the viscosity.

Thickening

A "thickening agent" according to the invention is defined as a compound capable of increasing the viscosity of the topical composition as defined herein. Suitable thickening agents are selected from one or more of compounds of polyacrylic acid (carbomer) or derivatives hereof or other fast gelling polymers e.g. hyaluronic acid, gelatine, pectin and methylcellulose. Preferred thickening agents are selected from one or more of polymers, carbomer, poloxamer, PEG/macrogol and/or carboxylic acid. In an even more preferred embodiment, thickening agents are selected from one or more types of acrylic acid and C10-30 alkyl acrylate co-monomer and crosslinked polyacrylic acid copolymer.

Carbomer solutions possess an important characteristic i.e. they have the ability to absorb and retain water and swell to many times their original volume. The degree of swelling is dependent on solution pH, so that the gelling occurs when the pH increases above a certain point, dependent on the particular carbomer used. Thus, if the topical composition of the present invention comprises a carbomer and a pH where it swells, said topical composition will have a viscosity that makes it suitable for topical application.

Poloxamer solutions have an important characteristic i.e. they demonstrate temperature dependent self-assembling and thermo-gelling behaviour. This means that aqueous solutions of poloxamers are liquid at low temperature and form a gel at higher temperature in a reversible process. Thus, if the topical composition of the present invention comprises a poloxamer, said topical composition will have a low viscosity when the temperature is low, e.g. if keeping the topical composition in the refrigerator. Likewise, if the said topical composition is kept at room temperature, said topical composition will have a viscosity that makes it suitable for topical application.

In a preferred embodiment, the one or more thickening agent is present in the water miscible solvent, optionally with adjusted pH. In an even more preferred embodiment, the one or more thickening agent is one or more of a carbomer present in the water miscible solvent. In an alternative embodiment, the one or more thickening agent is one or more of a poloxamer present in the water miscible solvent.

Device

In the present context, the "device" is intended to mean a combination of a housing element for storing the topical composition of the present invention and a delivery element for delivering the topical composition of the present invention to a user of the device.

The delivering element may be a removable screw lid, tightly connected to the housing element. Thus, in some embodiments, the delivering element is configured in a way so it can be screwed onto the housing element e.g. via a re-attachable lid with is an integrated part of the housing element. In a preferred embodiment said housing element is an aluminum tube and the lid is a re-attachable plastic lid. In some embodiments, the delivering element is configured in a way so it can be pushed onto the housing element (push fit). In some embodiments, the delivering element is configured in a way so it can be hinged onto the housing element.

The housing element provides protection of the topical composition inside the housing element from being in contact with the surroundings. Thus, the housing element protects the topical composition from contaminants from the environment and prevent leakage of its contents to the surroundings.

In embodiments of the invention, the housing element and/or delivering element is made from suitable materials, such as rubber, plastic, glass or metal, such as aluminium or steel. The materials may also have been coated e.g. a metal with a heat resistant coating, such as a rubber or plastic coating. The housing material and/or delivering element may also be a sachet, an ampule or the like. In an embodiment, wherein said housing element is selected from an ampule, a sachet or the like, there is no separate delivery element in the device, and therefore the housing element is the delivery device on its own. This means that the sachet, ampule or the like is simply opened and the contents delivered through the opening.

The housing element and/or delivering element may have a height of less than 20 cm, such as less than 15 cm, preferably less than 12 cm, such as less than 10 cm, such as less than 8 cm, such as less than 6 cm, such as less than 4 cm and a diameter of less than 6 cm, such as less than 5 cm, such as less than 4 cm, such as less than 2 cm, and a volume of about 1 L, such as about 800 ml, such as about 600 ml, such as about 400 ml, such as about 200 ml, such as about 150 ml, such as about 100 ml, such as about 75 ml, such as about 50 ml, such as about 25 ml, such as about 20 ml, such as about 15 ml, such as about 5 ml.

Unless defined otherwise, all technical and scientific terms used herein have the same meaning as commonly understood by persons skilled in the art. Although any methods and materials equivalent or similar to those described herein can be used in the practice of the present disclosure, typical methods and materials are described. All methods described herein can be performed in any suitable order unless otherwise indicated herein or otherwise clearly contradicted by context.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Overview of Examples

Examples 1.1-1.4: Production and stability of ointment comprising probiotic bacteria.

Example 2: Stability of commercial product comprising bacteria.

Materials and methods:

An overview of the excipients and equipment used is shown in Table 1, and the types of probiotic bacteria used are shown in Table 2.

The probiotic bacteria used were *Lactobacillus rhamnosus*, *Lactobacillus paracasei*, and *Bifidobacterium animalis* subsp *lactis*. ESSE® Sensitive Serum from ESSE® skincare was purchased via the internet. ESSE® Probiotic Serum from ESSE® skincare was purchased from a store in Copenhagen, Denmark.

TABLE 1

Excipients and equipment

| Brand name | Type | Type | Company |
|---|---|---|---|
| Paraffin oil | Oil | Paraffin oil | Henry Lamotte |
| High Oleic Sunflower Oil | Oil | High Oleic Sunflower Oil | AAK |
| MCOLORPHAST ™ | pH-indicator strips 2.0-9.0 | pH-indicator strips 2.0-9.0 | Merck KGaA |
| Caprylic/capric/myristic/stearic triglyceride-SOFTISAN ® 378 | Hard fat | Hard fat | IOI OLEOCHEMICAL |
| Hard fat-WITEPSOL ® E85 | Hard fat | Hard fat | IOI OLEOCHEMICAL |
| Hard fat-WITEPSOL ® H32 (app. 85% Triglycerides & up to 15% diglycerides | Hard fat | Hard fat | IOI OLEOCHEMICAL |
| GELEOL ™ pellets (glyceryl palmitostearate) | glyceryl palmitostearate | glyceryl palmitostearate | GatteFosse |
| COMPRITOL ® 888 CG Pellets (glyceryl dibehenate) | glyceryl dibehenate | glyceryl dibehenate | GatteFosse |
| Carnauba wax | Wax | Wax | Strahl & Pitsch Inc |
| ESSE ® Sensitive Serum | Commercial product, ESSE ® Sensitive Serum (Batch 16AXCE, exp. September 2018). | Jojoba seed oil, sesame seed oil, hydrogenated vegetable oil, shea butter, isoamyl laurate, *lactobacillus*, tocopherol, sunflower seed oil, ascorbyl palmitate, vanillin, gamma decalactone | ESSE ® skincare |
| ESSE ® Probiotic Serum | Commercial product, ESSE ® Probiotic Serum (Batch 18ADF, exp. August 2019) | Jojoba seed oil, sesame seed oil, shea butter, hydrogenated vegetable oil, isoamyl laurate, Marula Seed Oil *lactobacillus*, tocopherol sunflower seed oil,, ascorbyl palmitate, vanillin, gamma decalactone | ESSE ® skincare |

TABLE 2

| | Bacteria | | |
|---|---|---|---|
| Type | Brand name | Deposited as No. | Company |
| *Lactobacillus rhamnosus* | LGG ® | ATCC 53103 | Chr. Hansen |
| *Lactobacillus paracasei* | F19 ® | LMG-P-17806 | Chr. Hansen |
| *Bifidobacterium animalis* subsp *lactis* | BB-12 ® | DSM 15954 | Chr. Hansen |

Example 1—Production and Stability of Ointment Comprising Probiotic Bacteria

The below table shows the compositions of the trial batches produced in examples 1.1-1.4.

TABLE 3

Composition of the trial batches produced

| Example No. | 1.1 | 1.2 | 1.3 | 1.4 |
|---|---|---|---|---|
| Ingredients in mg or g per batch (%, g/100 g gel product) | | | | |
| *Lactobacillus rhamnosus* | 1788.5 mg (4.4%) | | | 17.3 g (2.0%) |
| *Lactobacillus paracasei* | | 3.6 g (3.6%) | | |
| *Bifidobacterium animalis* subsp lactis | | | 3.5 g | 14.1 g (1.7%) |
| caprylic/capric/myristic/stearic triglyceride-SOFTISAN ® 378 | 12.51 g (28.8%) | 28.9 g | 30.5 g | |
| Hard fat-WITEPSOL ® E85 | 12.51 g (28.8%) | 28.9 g | 30.5 g | |
| Hard fat-WITEPSOL ® H32 | 4.16 g (9.6%) | 9.7 g | 10 g | |
| High oleic acid sunflower oil | 12.54 g (28.8%) | | | |
| Liquid paraffin | | 28.9 g | 30.5 g | 652.6 g (77%) |
| GELEOL ™ Pellets (glyceryl palmitostearate) | | | | 73.4 g (8.7%) |
| COMPRITOL ® 888 CG Pellets (glyceryl dibehenate) | | | | 73.4 g (8.7%) |
| Carnauba Wax | | | | 16.3 g (1.9%) |
| Total weight of ingredients | 43.48 g (100%) | 100 g | 105 g | 847.1 g |

Example 1.1—Production and Stability of an Ointment Comprising *Lactobacillus Rhamnosus*

Freeze dried *Lactobacillus rhamnosus* is grinded and afterwards sieved using a 200 μm sieve and stored at −20° C. The powder is acclimatized before it is used for further suspending in the lipid phase. The hard fats and the caprylic/capric/myristic/stearic triglyceride and the high oleic sunflower oil is added to a glass beaker heated to about 45-50° C. for complete melt and mixing, and stirred slowly until cooled to below 30° C. The grinded freeze-dried *Lactobacillus rhamnosus* having a diameter of no more than 200 μm was introduced into the ointment at room temperature using mortar and pistil. The amounts of bacteria and ingredients used for Example 1.1 are found in Table 3.

The full trial batch of 43.48 g ointment is immediately portioned onto plastic trays, packed into aluminum pouched 12.5×16 cm, flushed with nitrogen and heat sealed. Each aluminum pouch contains approximately 8 g. The aluminum pouches are right after production placed temperature and humidity controlled chamber of 25° C.±3° C./60±5% RH. At time point 0, 1, 3, 6 and 10 months aluminum pouches are withdrawn from the climatic chambers and the total viable cell count of *Lactobacillus rhamnosus* is determined as Colony Forming Units per g ointment product (CFU/g) by a pour plate method with MRS Agar pH 6.2 (Oxoid CM0361). Triplicates of 2 g product are mixed with 198 g pre-heated (45° C.) Maximum Recovery Diluent (MRD) (e.g. Oxoid CM0733) with added 1% Tween 80 preparing a 1:100 dilution using a laboratory blender (e.g. SMASHER®, bioMerieux) for 2 minutes at 450-550 strokes per minute. A serial dilution in MRD is prepared for each weighing and two dilutions/volumes meeting 30-300 CFU/plate are used (2×2 plates for each weighing). The plates are incubated under anaerobic conditions at 37° C. for 3 days. The colonies are counted and the result is calculated as the average of the results for the three weighings in CFU/g. The results from the stability setup are found in Table 4 and FIG. 1A.

TABLE 4

Comparison of the CFU values obtained within the stability study of the ointment comprising *Lactobacillus rhamnosus* in the ointment of example 1.1.

| Time, months | Colony Forming Units (CFU)/g 25° C./60% RH |
|---|---|
| 0 | 1.2E+10 |
| 1 | 1.0E+10 |
| 3 | 9.9E+09 |
| 6 | 8.6E+09 |
| 10 | 8.8E+09 |

Conclusions from Example 1.1

The results are presented in FIG. 1A and shows stability of 4.4% *Lactobacillus rhamnosus* in a topical composition (ointment) of the present invention at 25° C.±3° C./60±5% RH. It is evident that the stability of the lipophilic ointment produced showed only limited loss of viable cells through the storage period up to months when stored at 25° C./60% RH. i.e. a topical composition of the present invention comprising *Lactobacillus rhamnosus* at 25° C.±3° C./60±5% RH is surprisingly stable, as an amount of at least $10^9$ CFU/g of said *Lactobacillus rhamnosus* is viable even at 10 months. The decrease in viable cells is promising for a commercial product with a shelf life of 2 years at 25° C./60% RH.

Hence, it has been shown that the topical composition of the present invention is able to keep the probiotic bacteria *Lactobacillus rhamnosus* viable for a surprisingly long time i.e. at least 10 months at 25° C.±3° C./60±5% RH as only a surprisingly limited loss of viable cells through the storage period up to 10 months was observed.

Example 1.2—Production and Stability of an Ointment Comprising *Lactobacillus paracasei*

Freeze dried *Lactobacillus paracasei* is grinded and afterwards sieved using a 200 μm sieve and stored at −20° C. The powder is acclimatized before it is used for further suspending in the lipid phase. The hard fats and the caprylic/capric/myristic/stearic triglyceride and the liquid paraffin is added to a glass beaker heated to about 45-50° C. for complete melt and mixing, and stirred slowly until cooled to below 30° C. The grinded freeze-dried *Lactobacillus paracasei* having a diameter of no more than 200 μm was introduced into the ointment at room temperature using mortar and pistil. The amounts of bacteria and ingredients used for Example 1.2 are found in Table 3.

The full trial batch of 100 g ointment is immediately portioned onto plastic trays, packed into aluminum pouched 12.5×16 cm, flushed with nitrogen and heat sealed. Each aluminum pouch contains approximately 7 g. The aluminum pouches are right after production placed in either a temperature and humidity controlled chamber of 25° C.±3° C./60±5% RH or in a refrigerator at 5° C.±3° C. At time point 0, 1 and 3 months (25° C./60% RH) and t=0 month (5° C.) aluminum pouches are withdrawn from the climatic chambers and the total cell count of *Lactobacillus paracasei*, is determined as Colonic Forming Units per g ointment product (CFU/g). The total viable cell count of *Lactobacillus paracasei* was determined as Colony Forming Units per g ointment product (CFU/g) by a pour plate method with MRS Agar pH 6.2 (Oxoid CM0361). Triplicates of 2 g product are mixed with 198 g pre-heated (45° C.) Maximum Recovery Diluent (MRD) (e.g. Oxoid CM0733) with added 1% Tween 80 preparing a 1:100 dilution using a laboratory blender (e.g. SMASHER®, bioMerieux) for 2 minutes at 450-550 strokes per minute. A serial dilution in MRD is prepared for each weighing and two dilutions/volumes meeting 30-300 CFU/plate are used (2×2 plates for each weighing). The plates are incubated under anaerobic conditions at 37° C. for 3 days. The colonies are counted and the result is calculated as the average of the results for the three weighings in CFU/g. The results from the stability setup are found in Table 5 and FIG. 1B and FIG. 1C.

The viscosity is measured to app. 75 000 mPa·s using a shear rate of 2.0 s$^{-1}$ at 25° C. The viscosity is measured to app. 18 000 mPa·s using a shear rate of 2.0 s$^{-1}$ at 34° C.

TABLE 5

Comparison of the CFU values obtained from the stability study of *Lactobacillus paracasei*, in the ointment of example 1.2.

| Time, months | Colony Forming Units per g (CFU/g) | |
| --- | --- | --- |
| | 5° C. | 25° C./60% RH |
| 0 | 1.7E+10 | 1.7E+10 |
| 1 | NA | 1.6E+10 |
| 3 | NA | 1.1E+10 |
| 6 | NA | 8.3E+9 |
| 16 | 1.8E+10 | 2.4E+9 |

NA: Not available

Conclusions from Example 1.2

Figure 1B:
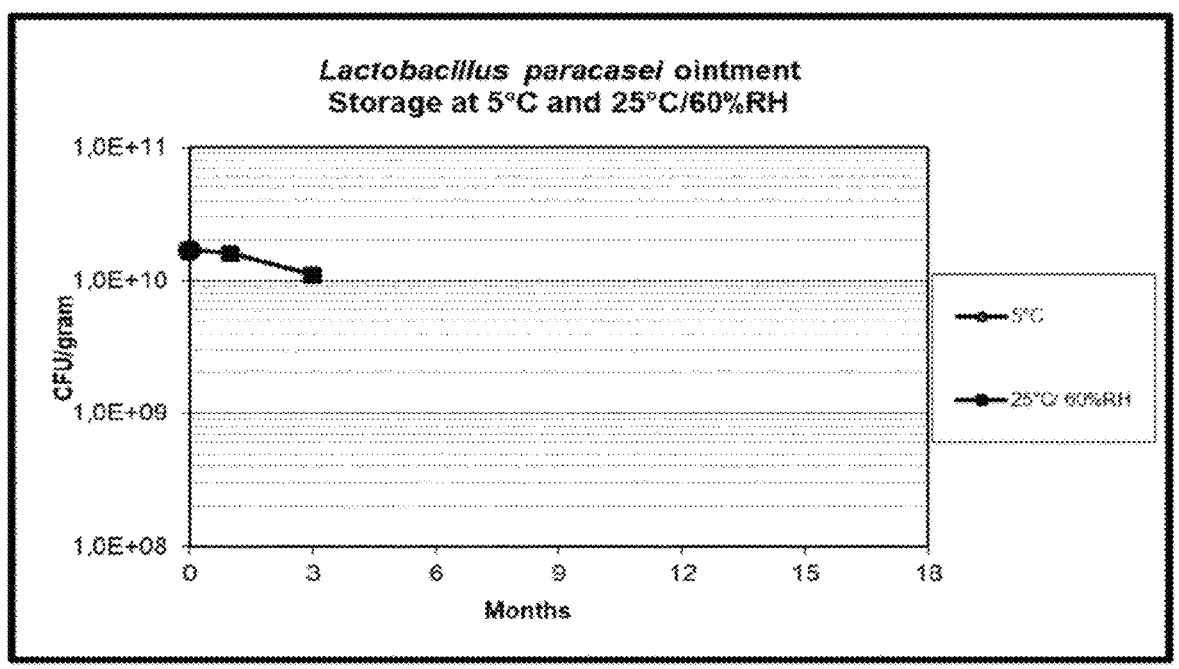
FIG. 1B and FIG. 1C show stability of an ointment comprising *Lactobacillus paracasei* at 25° C.±3° C./60±5% RH and at 5° C.
Figure 1C:
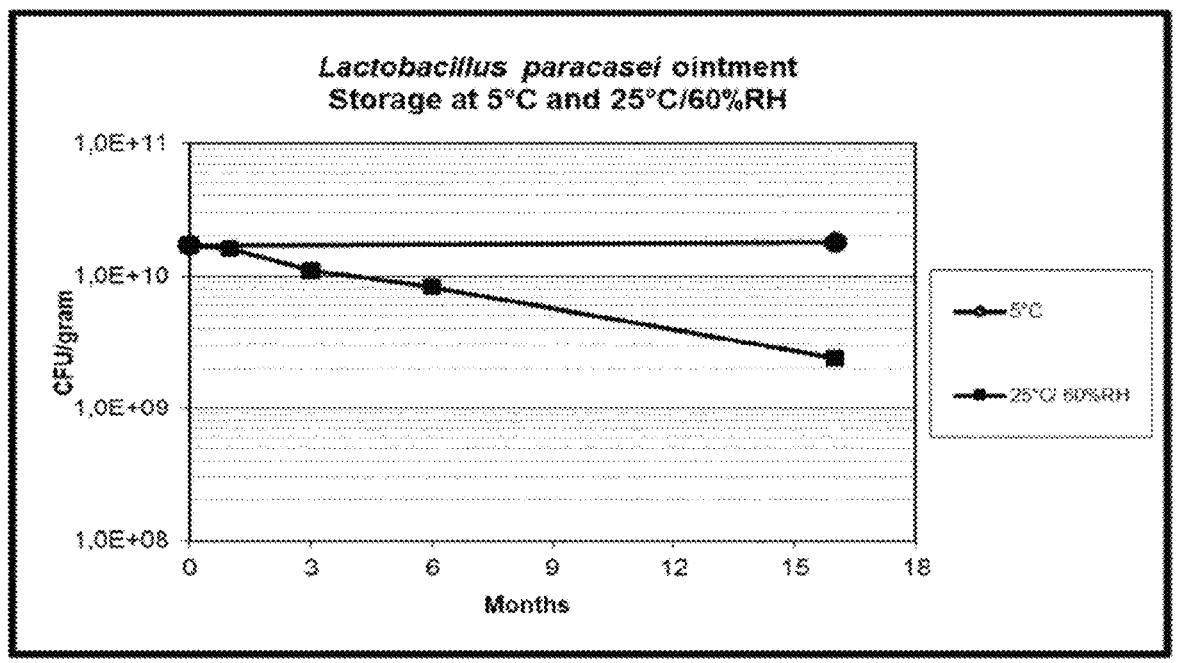

The results are presented in FIG. 1B and FIG. 1C and show stability of 3.6% *Lactobacillus paracasei* in a topical composition (ointment) of the present invention at 25° C.±3° C./60±5% RH and 5° C.±3° C. It is evident that the stability of the lipophilic ointment produced showed only limited loss of viable cells through the storage period up to 16 months when stored at 25° C./60% RH and that a topical composition of the present invention comprising *Lactobacillus paracasei* when kept at 25° C.±3° C./60±5% RH is surprisingly stable, as an amount of at least 10$^9$ CFU/g of said *Lactobacillus paracasei* is viable even at 16 months and an amount of at least 10$^{10}$ CFU/g of said *Lactobacillus paracasei* is viable even at 16 months at 5° C.±3° C. The decrease in viable cells is promising for a commercial product with a shelf life of 2 years at 25° C./60% RH.

Hence, it has been shown that the topical composition of the present invention is able to keep the probiotic bacteria *Lactobacillus paracasei* viable for a long time, i.e. at least 16 months at 25° C.±3° C./60±5% RH or 5° C., as only a surprisingly limited loss of viable cells through the storage period up to 16 months was observed.

The limited decrease in viable cells is surprising and very promising for a commercial product comprising a topical composition of the invention with a shelf life of 2 years at 25° C./60% RH or 5° C.

Example 1.3—Production of an Ointment Comprising *Bifidobacterium animalis* Subsp *Lactis* in the Ointment of Example 3

Freeze dried *Bifidobacterium animalis* subsp *lactis* is grinded and afterwards sieved using a 200 μm sieve and stored at −20° C. The powder is acclimatized before it is used for further suspending in the lipid phase. The hard fats and the caprylic/capric/myristic/stearic triglyceride and the liquid paraffin is added to a glass beaker and heated to about 45-50° C. for complete melt and mixing, and stirred slowly until cooled to below 30° C. The grinded freeze-dried *Bifidobacterium animalis* subsp *lactis* having a diameter of no more than 200 μm is introduced into the ointment at room temperature using mortar and pistil. The amounts of bacteria and ingredients used for Example 1.3 are found in Table 3.

The full trial batch of 105 g ointment is immediately portioned onto plastic trays, packed into aluminum pouched 12.5×16 cm, flushed with nitrogen and heat sealed. Each aluminum pouch contains approximately 7 g. The aluminum pouches are right after production placed in either a temperature and humidity controlled chamber of 25° C.±3° C./60±5% RH or in a refrigerator at 5° C.±3° C. At time point 0, 1 and 3 months (25° C./60% RH) and t=0 month (5° C.) aluminum pouches are withdrawn from the climatic chambers and the total cell count of *Bifidobacterium animalis* subsp *lactis*, is determined as Colonic Forming Units per g ointment product (CFU/g). The total viable cell count of *Bifidobacterium animalis* subsp *lactis* is determined as Colony Forming Units per g ointment product (CFU/g) by a pour plate method with MRS Agar pH 6.2 (Oxoid CM0361) with added 0.05% Cysteine, HCl (Merck 102839). Triplicates of 2 g product are mixed with 198 g pre-heated (45° C.) Maximum Recovery Diluent (MRD) (e.g. Oxoid CM0733) with added 1% Tween 80 preparing a 1:100 dilution using a laboratory blender (e.g. SMASHER®, bioMerieux) for 2 minutes at 450-550 strokes per minute. A serial dilution in MRD is prepared for each weighing and two dilutions/volumes meeting 30-300 CFU/plate are used (2×2 plates for each weighing). The plates are incubated under anaerobic conditions at 37° C. for 3 days. The colonies are counted and the result is calculated as the average of the results for the three weighings in CFU/g. The results from the stability setup are found in Table 6 and FIG. 2A and FIG. 2B.

The viscosity is measured to app. 75 000 mPa·s using a shear rate of 2.0 s$^{-1}$ at 25° C. The viscosity is measured to app. 36 500 mPa·s using a shear rate of 2.0 s$^{-1}$ at 30° C.

TABLE 6

Comparison of the CFU values obtained within the stability study of the ointment comprising *Bifidobacterium animalis* subsp *lactis* in the ointment of example 1.3

| | Colony Forming Units per g (CFU/g) | |
|---|---|---|
| Time, months | 5° C. | 25° C./60% RH |
| 0 | 1.8E+10 | 1.8E+10 |
| 1 | NA | 2.10E+10 |
| 3 | NA | 2.0E+10 |
| 6 | NA | 1.8E+10 |
| 12 | 1.9E+10 | 1.7E+10 |

NA: Not available

Conclusions from Example 1.3

Figure 2A:
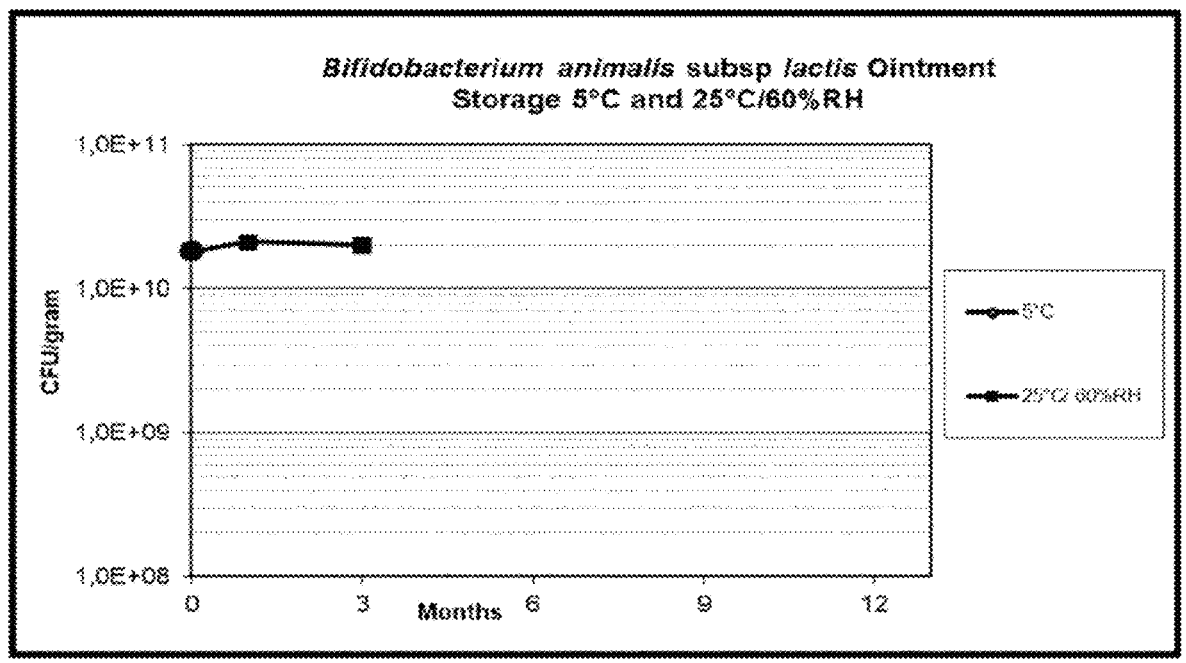
FIG. 2A and FIG. 2B show stability of an ointment comprising *Bifidobacterium animalis* subsp *lactis* at 25° C.±3° C./60±5% RH and at 5° C.
Figure 2B:
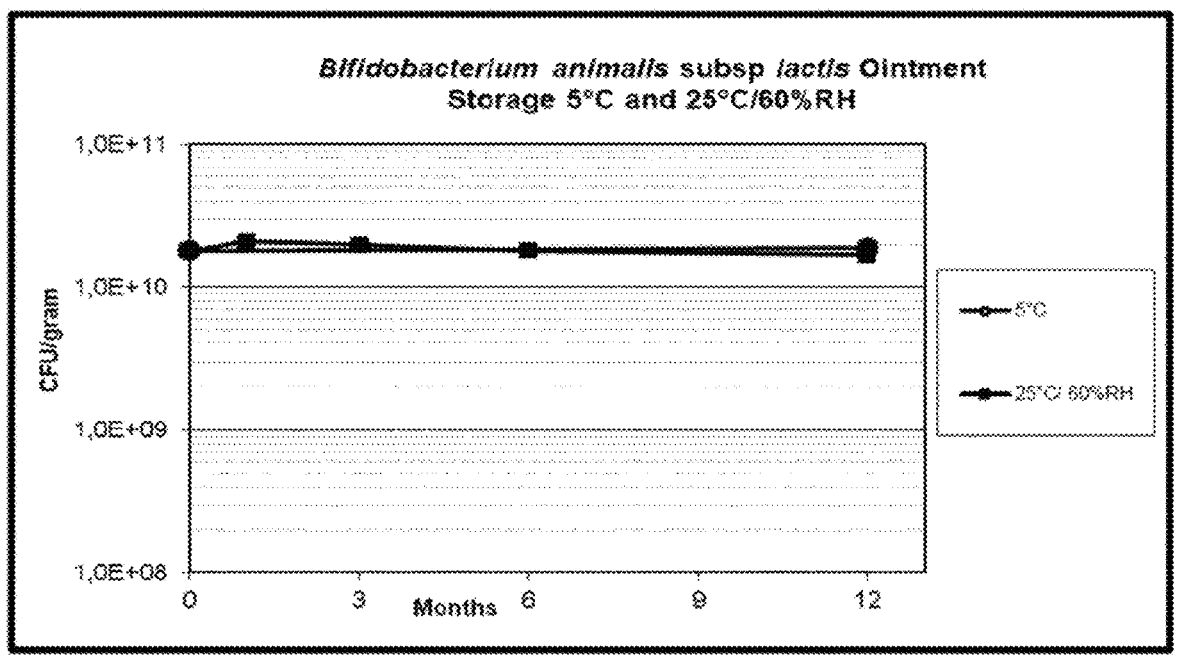

The results are presented in FIG. 2A and FIG. 2B show stability of *Bifidobacterium animalis* subsp *lactis* in a topical composition (ointment) of the present invention at 25° C.±3° C./60±5% RH and 5° C.±3° C. It is evident that the stability of the ointment produced showed no loss of viable cells through the storage period up to 12 months when stored at 25° C./60% RH. i.e. topical composition of the present invention comprising *Bifidobacterium animalis* subsp *lactis* at 25° C.±3° C./60±5% RH is very good, as an amount of at least $10^{10}$ CFU/g of said *Bifidobacterium animalis* subsp *lactis* are viable at 12 months. This is also observed for storage at 5° C. The non-existing decrease in viable cells is promising for a commercial product with a shelf life of 2 years at 25° C./60% RH.

Hence, it has been shown that the topical composition of the present invention is able to keep the probiotic bacteria *Bifidobacterium animalis* subsp *lactis* viable for a surprisingly long time i.e. at least 12 months at 25° C.±3° C./60±5% RH and 5° C. as no loss of viable cells through the storage period up to 12 months was observed.

The limited decrease in viable cells is surprising and very promising for a commercial product comprising a topical composition of the invention with a shelf life of 2 years at 25° C./60% RH or 5° C.

Example 1.4—Production and Stability of an Ointment Comprising *Lactobacillus rhamnosus* and *Bifidobacterium animalis* subsp *lactis*

*Lactobacillus rhamnosus* and *Bifidobacterium animalis* subsp *lactis* is grinded and afterwards sieved using a 200 μm sieve and stored at −20° C. The powders are acclimatized before they are used for further suspending in the lipid phase. Non-probiotic ingredients (paraffin, glyceryl dibehenate, glyceryl palmitostearate and carnauba wax) are heated to app. 85 C, under stirring, and when all ingredients are mixed and melted, the mixture is slowly cooled down under constant stirring). When the mixture is below 30° C., the grinded freeze-dried *Lactobacillus rhamnosus* and *Bifidobacterium animalis* subsp *lactis* having a diameter of no more than 200 μm was introduced into the ointment at room temperature using mortar and pistil, and stirred until a homogeneous mixture is obtained. The blend is filled into 10 ml plastic syringes for stability trial.

The full trial batch of 847.1 g ointment is immediately portioned onto plastic syringes closed with a cap and packed into aluminum pouches and heat sealed. Each syringe in aluminum pouch contains approximately 8 g. The syringe in aluminum pouches are right after production placed in a refrigerator at 5° C.±3° C. or in a temperature and humidity controlled chamber of 25° C.±3° C./60±5% RH. At time point 0 and 1 months (25° C./60% RH) and t=0 month (5° C.) aluminum pouches are withdrawn from the climatic chambers and the total cell count of *Lactobacillus rhamnosus* and *Bifidobacterium animalis* subsp *lactis* is determined as Colonic Forming Units per g ointment product (CFU/g) separately.

The total viable cell count of *Bifidobacterium animalis* subsp *lactis* is determined as Colony Forming Units per g ointment product (CFU/g) by a pour plate method with MRS Agar pH 6.2 (Oxoid CM0361) with added 0.05% Cysteine, HCl (Merck 102839) and 4 mg/l tetracyclin. Triplicates of 2 g product are mixed with 198 g pre-heated (45° C.) Maximum Recovery Diluent (MRD) (e.g. Oxoid CM0733) with added 1% Tween 80 preparing a 1:100 dilution using a laboratory blender (e.g. SMASHER®, bioMerieux) for 2 minutes at 450-550 strokes per minute. A serial dilution in MRD is prepared for each weighing and two dilutions/volumes meeting 30-300 CFU/plate are used (2×2 plates for each weighing). The plates are incubated under anaerobic conditions at 37° C. for 3 days. The colonies are counted and the result is calculated as the average of the results for the three weighings in CFU/g.

The total viable cell count of *Lactobacillus rhamnosus* is determined as Colony Forming Units per g ointment product (CFU/g) by a pour plate method with MRS Agar pH 6.2 (Oxoid CM0361). Triplicates of 2 g product are mixed with 198 g pre-heated (45° C.) Maximum Recovery Diluent (MRD) (e.g. Oxoid CM0733) with added 1% Tween 80 preparing a 1:100 dilution using a laboratory blender (e.g. SMASHER®, bioMerieux) for 2 minutes at 450-550 strokes per minute. A serial dilution in MRD is prepared for each weighing and two dilutions/volumes meeting 30-300 CFU/plate are used (2×2 plates for each weighing). The plates are incubated under aerobic conditions at 37° C. for 3 days. The colonies are counted and the result is calculated as the average of the results for the three weighings in CFU/g.

Figure 2C:
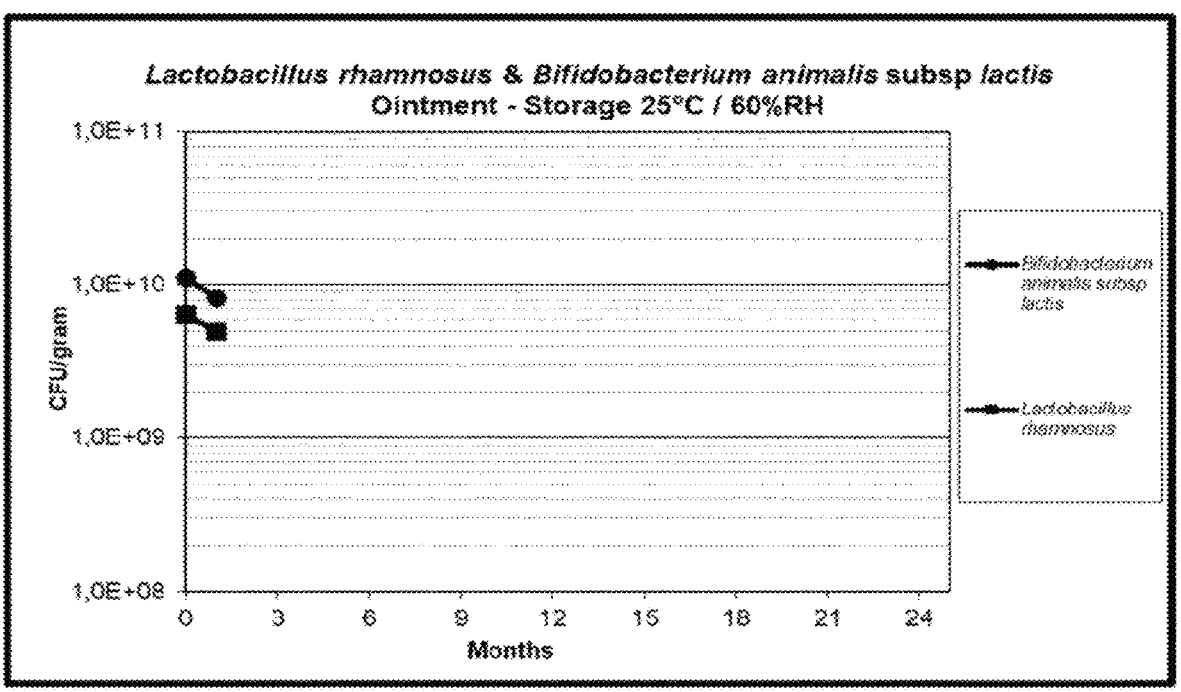
FIG. 2C and FIG. 2D show stability of an ointment comprising *Lactobacillus rhamnosus* and *Bifidobacterium animalis* subsp *lactis* at 25° C.±3° C./60±5% RH.
Figure 2D:
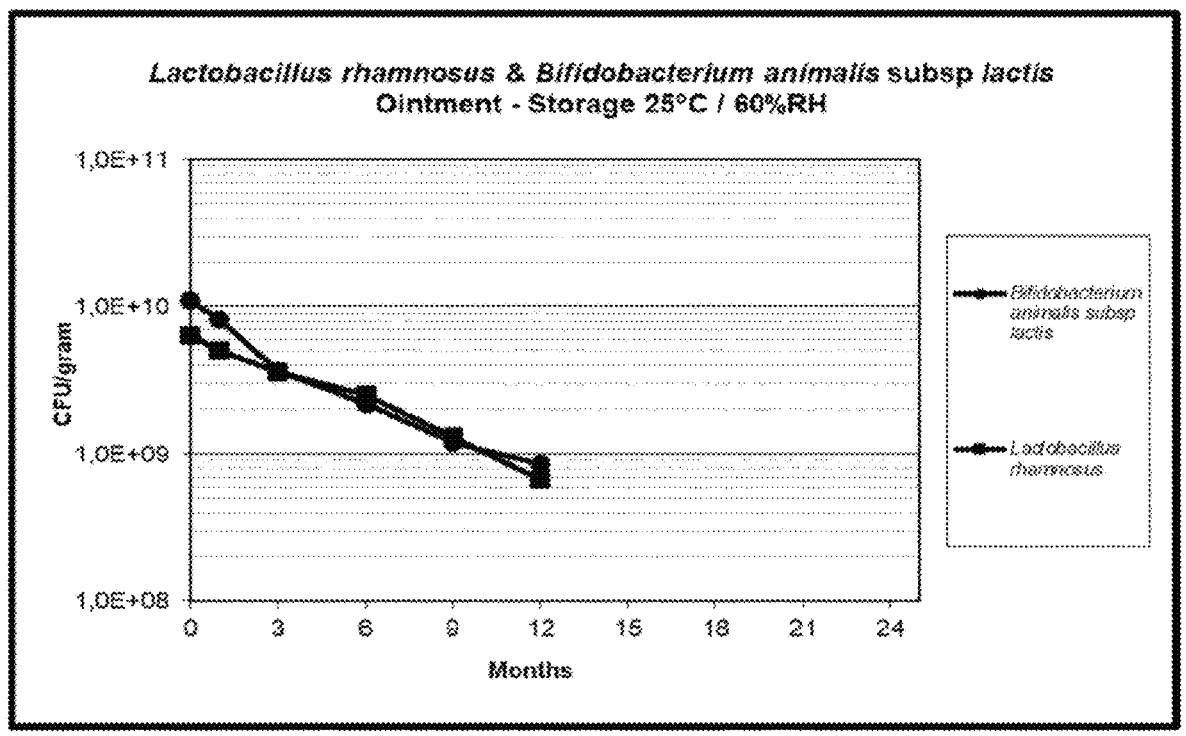

The results from the stability setup are found in Table 7 and FIG. 2C and FIG. 2D.

TABLE 7

Comparison of the CFU values obtained within the stability study of the ointment comprising *Bifidobacterium animalis* subsp *lactis* and *Lactobacillus rhamnosus* in the ointment of example 1.4 at 25° C./60% RH.

| | Colony Forming Units per g (CFU/g) 25° C./60% RH | |
|---|---|---|
| Time, months | *Bifidobacterium animalis* subsp *lactis* | *Lactobacillus rhamnosus* |
| 0 | 1.1E+10 | 6.4E+09 |
| 1 | 8.2E+09 | 5.0E+09 |
| 3 | 3.7E+09 | 3.6E+09 |
| 6 | 2.2E+09 | 2.5E+09 |
| 9 | 1.2E+09 | 1.3E+09 |
| 12 | 8.6E+08 | 6.8E+08 |

Figure 3A:
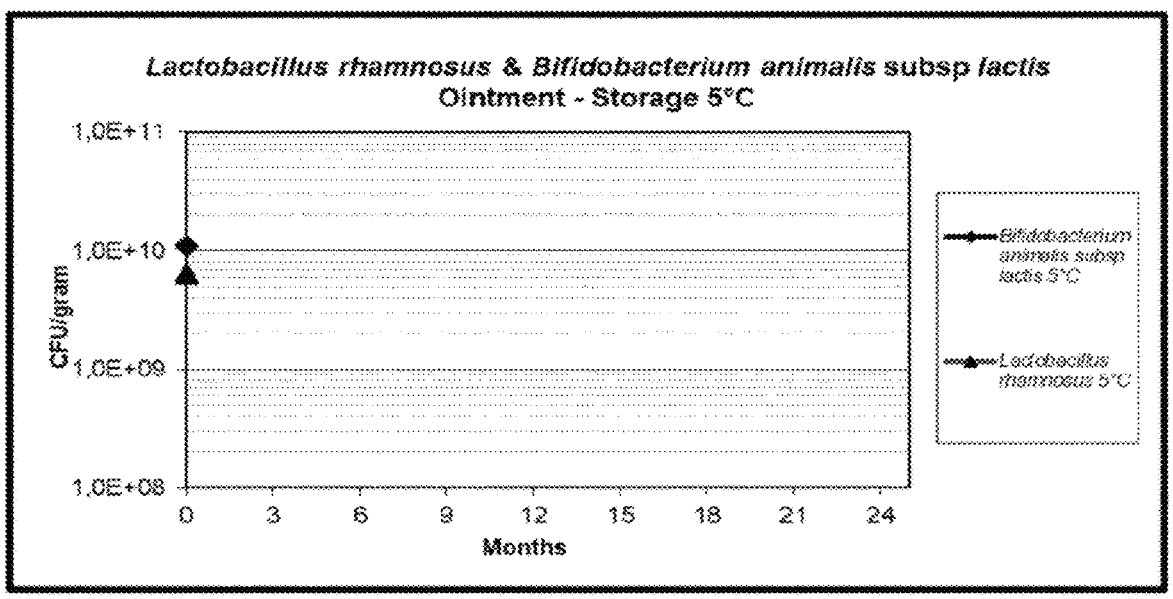
FIG. 3A and FIG. 3B show stability of an ointment comprising *Lactobacillus rhamnosus* and *Bifidobacterium animalis* subsp *lactis* at 5° C.
Figure 3B:
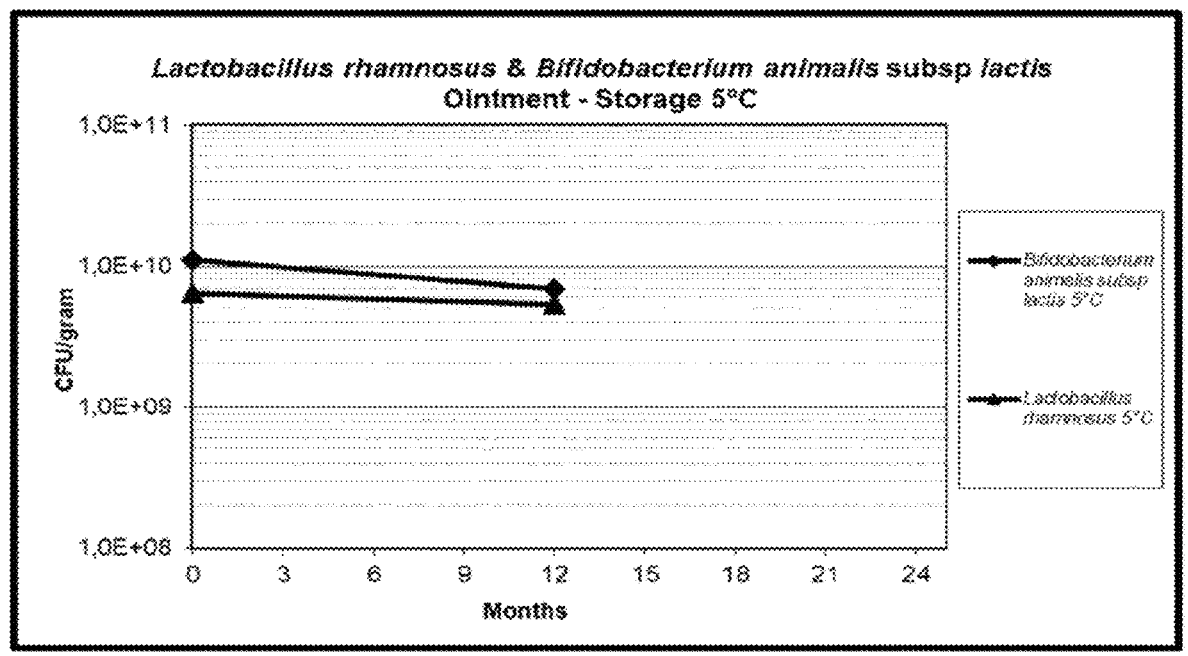

The results from the stability setup at 5° C. are found in Table 8 and FIG. 3A and FIG. 3B.

TABLE 8

Comparison of the CFU values obtained within the stability study of the ointment comprising *Bifidobacterium animalis* subsp *lactis* and *Lactobacillus rhamnosus* in the ointment of example 1.4 at 5° C.

| | Colony Forming Units per g (CFU/g) 5° C. | |
|---|---|---|
| Time, months | *Bifidobacterium animalis* subsp *lactis* | *Lactobacillus rhamnosus* |
| 0 | 1.1E+10 | 6.4E+09 |
| 1 | NA | NA |
| 3 | NA | NA |
| 6 | NA | NA |
| 9 | NA | NA |
| 12 | 6.8E+09 | 5.3E+09 |

NA: Not available

Figure 3C:
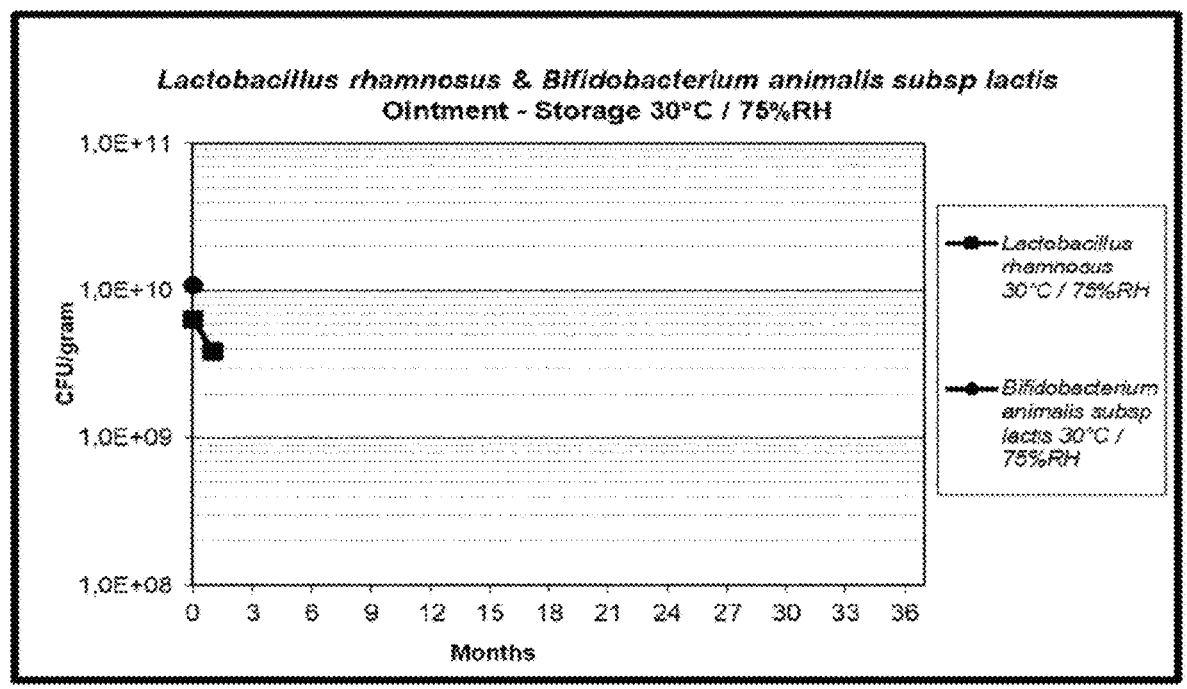
FIG. 3C and FIG. 3D show stability of an ointment comprising *Lactobacillus rhamnosus* and *Bifidobacterium animalis* subsp *lactis* at 30° C./75% RH.
Figure 3D:
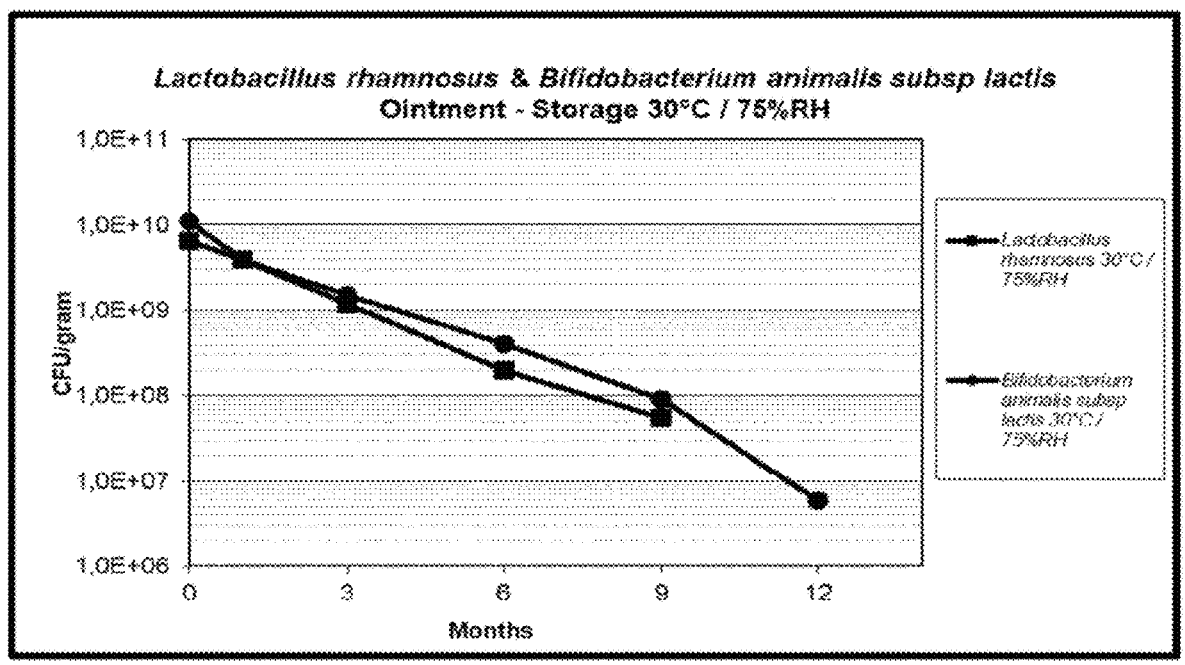

The results from the stability setup at 30° C. are found in Table 9 and FIG. 3C and FIG. 3D.

TABLE 9

Comparison of the CFU values obtained within the stability study of the ointment comprising *Bifidobacterium animalis* subsp *lactis* and *Lactobacillus rhamnosus* in the ointment of example 1.4 at 30° C./75% RH.

| | Colony Forming Units per g (CFU/g) 30° C./75% RH | |
|---|---|---|
| Time, Months | *Bifidobacterium animalis* subsp *lactis* | *Lactobacillus rhamnosus* |
| 0 | 1.1E+10 | 6.4E+09 |
| 1 | 3.9E+9 | 3.9E+09 |
| 3 | 1.5E+09 | 1.2E+09 |
| 6 | 4.1E+08 | 2.0E+08 |
| 9 | 9.1E+07 | 5.5E+07 |
| 12 | 6.0E+06 | NA |

NA: Not available

Conclusions from Example 1.4

The results presented in FIG. 3A and FIG. 3B show stability of 2.0% *Lactobacillus rhamnosus* and 1.7% *Bifidobacterium animalis* subsp *lactis* in a topical ointment of the present invention at 5° C., t=12 month. It is evident that the stability of the ointment produced showed limited loss of viable cells during the manufacturing as a period up to 12 months when stored at 5° C. showed a remarkable high amount of at least $1\times10^9$ CFU/g of said *Lactobacillus rhamnosus* and *Bifidobacterium animalis* subsp *lactis* being viable after production at 12 month.

Further results are presented in FIG. 2C and FIG. 2D and FIG. 3C and FIG. 3D which show stability of 2.0% *Lactobacillus rhamnosus* and 1.7% *Bifidobacterium animalis* subsp *lactis* in a topical ointment of the present invention at 25° C.±3° C./60±5% RH and 30° C.±3° C./75±5% RH. It is evident that the stability of the ointment produced showed limited loss of viable cells through the storage period up to 12 month when stored at 25° C./60% RH or 30° C./75% RH at 6 M, i.e. the topical composition of the present invention comprising *Lactobacillus rhamnosus* and *Bifidobacterium animalis* subsp *lactis* at 25° C./60% RH is very good, as an amount of at least $1\times10^8$ CFU/g of said *Lactobacillus rhamnosus* and *Bifidobacterium animalis* subsp *lactis* are viable at 12 month and the topical composition of the present invention comprising *Lactobacillus rhamnosus* and *Bifidobacterium anima/is* subsp *lactis* at 30° C./75% RH is also very good, as an amount of at least $1\times10^8$ CFU/g of said *Lactobacillus rhamnosus* and *Bifidobacterium animalis* subsp *lactis* are viable at 6 month.

Hence, it has been shown that the topical composition of the present invention is able to keep the probiotic bacteria *Lactobacillus rhamnosus* and *Bifidobacterium anima/is* subsp *lactis* viable for a surprisingly long time i.e. at least 12 month at 25° C./60% RH or at least 6 month at 30° C./75% RH as limited loss of viable cells through the storage period up to 12 or 6 months, respectively was observed. The minor decrease in both viable cells is promising for a commercial product having a shelf life of 2 years at 25° C./60% RH or 5° C.

Example 2—Determination of Viable Bacteria Cells of *Lactobacillus* in Commercial Product Commercial products with claimed viable *Lactobacillus* have also been evaluated with respect to Colony Forming Units per g. The commercial product ESSE® sensitive serum (Batch 16AXCE) from ESSE® skincare was purchased via internet and comprises jojoba seed oil, sesame seed oil, hydrogenated vegetable oil, shea butter, isoamyl laurate, *lactobacillus*, tocopherol, sunflower seed oil, ascorbyl palmitate, vanillin, gamma decalactone. The commercial product has been purchased, stored as recommended until evaluation, and evaluated within the assigned product shelf life.

The total viable cell count of *Lactobacillus* is determined as Colony Forming Units per g product (CFU/g) by a pour plate method with MRS Agar pH 6.2 (Oxoid CM0361). The total viable cell count is determined as Colony Forming Units per g product (CFU/g) by a spread plate method on the surface of Tryptone Soy agar with sheep blood. 1.58 g product is mixed with 160.43 g pre-heated (45° C.) Maximum Recovery Diluent (MRD) (e.g. Oxoid CM0733) with added 1% Tween 80 preparing a 1:100 dilution using a laboratory blender (e.g. SMASHER®, bioMerieux) for 2 minutes at 450-550 strokes per minute. A serial dilution in MRD is prepared and two dilutions/volumes meeting 30-300 CFU/plate are used on the 2 plates (3×2×2 plates). The MRS Agar pH 6.2 plates are incubated under anaerobic conditions at 37° C. for 3 days. The Tryptone Soy agar with sheep blood plates are incubated under either aerobic or anaerobic conditions at 37° C. for 4 days. The colonies are counted and the result is calculated as CFU/g.

Another commercial product with claimed viable *Lactobacillus* has also been evaluated with respect to Colony Forming Units per g. The commercial product "ESSE® Probiotic Serum" (Batch 18ADF) from ESSE® skincare was purchased in a store in Copenhagen and stored as recommended until evaluation and evaluated within the assigned product shelf life. ESSE® Probiotic Serum comprises jojoba seed oil, sesame seed oil, hydrogenated vegetable oil, shea butter, isoamyl laurate, marula seed oil, *lactobacillus*, tocopherol, sunflower seed oil, ascorbyl palmitate, vanillin, gamma decalactone, i.e. the same ingredients as ESSE® Probiotic Serum except for marula seed oil.

The total viable cell count of *Lactobacillus* is determined as Colony Forming Units per g product (CFU/g) by a pour plate method with MRS Agar pH 6.2 (Oxoid CM0361). 1.58 g product is mixed with 160.43 g pre-heated (30° C.) Maximum Recovery Diluent (MRD) (e.g. Oxoid CM0733) with added 1% Tween 80 preparing a 1:100 dilution using a laboratory blender (e.g. SMASHER®, bioMerieux) for 2 minutes at 450-550 strokes per minute. A serial dilution in MRD is prepared and two dilutions/volumes meeting 30-300 CFU/plate are used on the 2 plates (3×2×2 plates). The MRS Agar pH 6.2 plates are incubated under anaerobic conditions at 37° C. for 3 days.

The total viable cell count is also determined as Colony Forming Units per g product (CFU/g) by a spread plate method on the surface of MRS agar. The products are applied directly on the surface of MRS agar plates and incubated, to investigate the presence of any colony forming Lactic acid bacteria. The product has not been exposed to any sample preparation i.e. heating and dilution. The MRS agar plates are divided into two groups and incubated under aerobic or anaerobic conditions at 37° C. for 3 days. The colonies are counted and the result is calculated as CFU/g.

No colonies are found neither on plates incubated under aerobic nor anaerobic conditions.

TABLE 10

Measured level of viable cells of *Lactobacillus* for commercial products

| | Pour plate method Colony Forming Units per g (CFU/g) | Spread plate method Colony Forming Units per g (CFU/g) |
|---|---|---|
| ESSE ® Sensitive Serum Batch 16AXCE Tested May 2017 (expiry date of product September 2018) | <1E+02 CFU/g Tested at 45° C. | <1E+02 CFU/g Tested at 45° C. |
| ESSE ® Probiotic Serum Batch 18ADF Tested June 2019 (expiry date of product August 2019) | <1E+02 CFU/g Tested at 30° C. | <1E+02 CFU/g Tested at 30° C. |

Conclusions from Example 2

The results from the evaluations of viability of *Lactobacillus* are given in Table 10. It is evident that the commercial products do not show any viable *Lactobacillus* at all i.e. that the commercial product allegedly comprising viable bacteria cells of *Lactobacillus* is not stable at all, not even from the moment of opening the container comprising the commercial product. It should be noted that the measurements of the commercial product were made well in advance of the expiry date of the product. In addition, it should be noted that using pre-heated (45° C.) Maximum Recovery Diluent (MRD) for the pour plate methods have been used in all examples of the present invention, and when testing ESSE® Sensitive Serum. Additional tests have been made using pre-heated (30° C.) Maximum Recovery Diluent (MRD) showing no difference i.e. ESSE® Sensitive Serum and ESSE® Probiotic Serum comprise no live bacteria i.e. <1E+02 CFU/g *Lactobacillus*.

Conclusion from Examples Section

The commercial products tested in Example 2 is products comprising *Lactobacillus* in a formulation made of primarily oils/fats/fatty acid esters, wherein no bacteria were viable. Thus, it is even more surprising that topical compositions of the present invention, being ointment formulation comprising oils/waxes and e.g. *Lactobacillus* demonstrates an amount of at least $10^9$ CFU/g of *Lactobacillus rhamnosus* being viable even at 10 months at 25° C. (example 1.1) or an amount of at least $10^{10}$ CFU/g of *Lactobacillus paracasei* being viable even at 16 months when stored at 5° C., and at least $10^9$ CFU/g of *Lactobacillus paracasei* being viable even at 16 months when stored at 25° C. (example 1.2).

It is also surprising that a topical composition of the present invention, being an ointment formulation comprising oils/waxes and e.g. *Bifidobacterium animalis* subsp *lactis* demonstrates an amount of at least $10^{10}$ CFU/g of *Bifidobacterium animalis* subsp *lactis* being viable even at 12 months when stored at 25° C. (example 1.3).

The invention claimed is:

1. A topical probiotic composition, comprising:
    viable probiotic bacteria of at least one probiotic bacterial strain selected from the genus *Lactobacillus* and *Bifidobacterium*, and
    at least one hydrophobic compound selected from anionic emulsifying wax, candelilla wax, carnauba wax, cetyl palmitate, cocoa butter, gum arabic, hard fat, microcrystalline wax, nonionic emulsifying wax, paraffin, shea butter, synthetic beeswax, white wax, xanthan gum, sunflower wax, monoglycerides, diglycerides, glyceryl behenate, glyceryl palmitostearate, glyceryl stearate, and caprylic, capric, myristic, and stearic triglycerides, and oils and waxes that are fluid at room temperature selected from ethyl oleate, evening primrose oil, grapeseed oil, hydrogenated vegetable oil, isopropyl isostearate, isopropyl myristate, isopropyl palmitate, jojoba oil, liquid lanolin, macademia oil, medium chain triglycerides, olive oil, paraffin oil, mineral oil, pomegranate oil, rapeseed oil, rice bran oil, rosehip oil, safflower oil, sesame oil, shea nut butter, soybean oil, sunflower oil, sweet almond oil, trimyristin, tripalmitin, tristearin, and avocado oil,
    wherein said viable probiotic bacteria have a water activity of no more than 0.30 and a diameter of no more than 300 µm;
    wherein, after storage for 1 day at 30° C. and 75% RH, the topical probiotic composition comprises at least $10^6$ CFU/g of said viable probiotic bacteria; and
    wherein the topical probiotic composition is formulated as a cream, drop, foam, gel, lotion, ointment, paste, poultice, salve, spray, thickened formulation, or unguent.

2. The topical probiotic composition of claim 1, wherein said viable probiotic bacteria are selected from a single strain or combination of strains of any of *Lactobacillus rhamnosus, Lactobacillus paracasei* and *Bifidobacterium animalis* subsp *lactis*.

3. The topical probiotic composition according to claim 1, wherein said at least one hydrophobic compound comprises:
    a hard fat, and
    one or more oils and waxes that are fluid at room temperature selected from ethyl oleate, evening primrose oil, grapeseed oil, hydrogenated vegetable oil, isopropyl isostearate, isopropyl myristate, isopropyl palmitate, jojoba (seed) oil, liquid lanolin, macademia oil, medium chain triglycerides, olive oil, paraffin oil, mineral oil, pomegranate oil, rapeseed oil, rice bran oil, rosehip oil, safflower oil, sesame oil, shea nut butter, soybean oil, sunflower oil, sweet almond oil, trimyristin, tripalmitin, tristearin, and avocado oil.

4. The topical probiotic composition according to claim 3, wherein said at least one hydrophobic compound comprises: (i) one or more of caprylic, capric, myristic, and stearic triglycerides, and (ii) paraffin oil.

5. The topical probiotic composition according to claim 1, wherein said at least one hydrophobic compound comprises one or more of caprylic, capric, myristic, and stearic triglycerides.

6. The topical probiotic composition according to claim 1, wherein said at least one hydrophobic compound comprises paraffin oil.

7. The topical probiotic composition according to claim 1, wherein said topical composition further comprises at least one active component selected from one or more of vitamins, minerals, antiseptics, preservatives, sun protection agents, and moisture sensitive agents.

8. The topical probiotic composition according to claim 1, wherein said topical composition comprises less than 5% (w/w) water.

9. A method of manufacturing the topical probiotic composition according to claim 1, comprising adding a dry composition comprising powdered viable probiotic bacteria of at least one probiotic bacterial strain selected from the genus *Lactobacillus* and *Bifidobacterium* and having a water activity of no more than 0.30 and a diameter of no more than 300 µm to at least one hydrophobic compound selected from anionic emulsifying wax, candelilla wax, carnauba wax, cetyl palmitate, cocoa butter, gum arabic, hard fat, microcrystalline wax, nonionic emulsifying wax, paraffin, shea butter, synthetic beeswax, white wax, xanthan gum, sunflower wax, monoglycerides, diglycerides, glyceryl behenate, glyceryl palmitostearate, glyceryl stearate, and caprylic, capric, myristic, and stearic triglycerides, and oils and waxes that are fluid at room temperature selected from ethyl oleate, evening primrose oil, grapeseed oil, hydrogenated vegetable oil, isopropyl isostearate, isopropyl myristate, isopropyl palmitate, jojoba oil, liquid lanolin, macademia oil, medium chain triglycerides, olive oil, paraffin oil, mineral oil, pomegranate oil, rapeseed oil, rice bran oil, rosehip oil, safflower oil, sesame oil, shea nut butter, soybean oil, sunflower oil, sweet almond oil, trimyristin, tripalmitin, tristearin, and avocado oil.

10. The method of claim 9, wherein said viable probiotic bacteria are selected from a single strain or combination of strains of any one of *Lactobacillus rhamnosus*, *Lactobacillus paracasei* and *Bifidobacterium animalis* subsp *lactis*.

11. The method of claim 9, wherein said topical probiotic composition comprises less than 5% (w/w) water.

12. The method of claim 9, wherein said at least one hydrophobic compound comprises:
a hard fat, and
one or more oils and waxes that are fluid at room temperature selected from ethyl oleate, evening primrose oil, grapeseed oil, hydrogenated vegetable oil, isopropyl isostearate, isopropyl myristate, isopropyl palmitate, jojoba oil, liquid lanolin, macadamia oil, medium chain triglycerides, olive oil, paraffin oil, mineral oil, pomegranate oil, rapeseed oil, rice bran oil, rosehip oil, safflower oil, sesame oil, shea nut butter, soybean oil, sunflower oil, sweet almond oil, trimyristin, tripalmitin, tristearin, and avocado oil.

13. The method of claim 9, wherein said hard fat comprises one or more selected from caprylic, capric, myristic, and stearic triglycerides.

14. The method of claim 9, wherein said at least one hydrophobic compound is paraffin.

15. A device containing the topical probiotic composition according to claim 1.

16. A method of administering probiotic bacteria, comprising applying the topical probiotic composition according to claim 1 to the skin of a subject in need thereof.

17. The topical probiotic composition according to claim 1, wherein the topical probiotic composition is formulated as a cream, an ointment, or a paste.

18. The topical probiotic composition according to claim 1, wherein the at least one hydrophobic compound is present at a concentration of at 80% w/w, relative to the total weight of the topical probiotic composition.

\* \* \* \* \*